United States Patent
Huber et al.

(10) Patent No.: US 8,501,734 B2
(45) Date of Patent: Aug. 6, 2013

(54) MEDICAL INTERVENTION IN HAEMATOLOGICAL CANCERS

(75) Inventors: Lukas Huber, Schwaz (AT); Simon Schnaiter, Kolsass (AT); Inge Tinhofer, Berlin (DE); Karin Jöhrer, Innsbruck (AT); Richard Greil, Salzburg (AT)

(73) Assignee: Oncotyrol-Center for Personalized Cancer Medicine GmbH (Ltd.), Innsbruck (AT)

( * ) Notice: Subject to any disclaimer, the term of this patent is extended or adjusted under 35 U.S.C. 154(b) by 143 days.

(21) Appl. No.: 12/994,491

(22) PCT Filed: May 26, 2009

(86) PCT No.: PCT/EP2009/003736
§ 371 (c)(1),
(2), (4) Date: Mar. 21, 2011

(87) PCT Pub. No.: WO2009/144009
PCT Pub. Date: Dec. 3, 2009

(65) Prior Publication Data
US 2011/0178076 A1    Jul. 21, 2011

(30) Foreign Application Priority Data
May 26, 2008  (EP) .................................... 08009559

(51) Int. Cl.
*A61K 31/535*    (2006.01)

(52) U.S. Cl.
USPC ...................... 514/229.8; 514/293; 514/250

(58) Field of Classification Search
USPC ...................... 514/229.8, 293, 250
See application file for complete search history.

(56) References Cited

U.S. PATENT DOCUMENTS
7,799,782 B2 * 9/2010 Munson et al. ............ 514/234.5
2006/0247188 A1  11/2006 Cheng et al.

FOREIGN PATENT DOCUMENTS
EP    1 889 609 A2    2/2008

OTHER PUBLICATIONS

International Search Report and Written Opinion received in the corresponding International Patent Application PCT/EP2009/003736, dated Aug. 6, 2009. (9 pgs.).
Coors, et al., "Topical imiquimod as treatment for different kinds of cutaneous lymphoma", *European Journal of Dermatology*, vol. 16, No. 4, 2006, pp. 391-393.
Hicks, et al., "Successful treatment of cutaneous chronic lymphocytic leukemia with a topical toll receptor 7/8 antagonist (Imiquimod)", *Blood*, vo. 104, No. 11, pt. 2, pp. 290B-291B, 2004.
Hideshima, et al., "Perifosine, an oral bioactive novel alkylphospholipid, inhibits Akt and induces in vitro and in vivo cytotoxicity in human multiple myeloma cells", *Blood*, vol. 107, No. 10, 2006, pp. 4053-4062.
Richardson, et al., "Multi-center phase II study of perifosine (KRX-0401) alone and in combination with dexamethasone (dex) for patients with relapsed or Relapsed/Refractory multiple myeloma (MM): Promising activity as combination therapy with manageable toxicity", *Blood*, vol. 110, No. 11, 2007, pp. 353A/1164A.
International Report on Patentability received in the corresponding International PCT Application No. PCT/EP2009/003736, dated Nov. 30, 2010.

* cited by examiner

*Primary Examiner* — Rei-tsang Shiao
(74) *Attorney, Agent, or Firm* — Foley & Lardner LLP

(57) ABSTRACT

The present invention relates to the medical and pharmaceutical use of substituted 1H-imidazo[4,5-c]quinolin-4-amines, in particular Imiquimod® and Gardiquimod®, alone or preferably in combination with Akt inhibitors, in particular with Akti1/2 and AktX, and most preferably with Akti1/2, in the treatment, prevention and/or amelioration of haematological cancers, in particular multiple myeloma disorders or B-cell disorders, and most particular in the therapy of multiple myeloma.

10 Claims, 8 Drawing Sheets

A

B

A

B

MEDICAL INTERVENTION IN HAEMATOLOGICAL CANCERS

CROSS-REFERENCE TO RELATED PATENT APPLICATIONS

Figure 1:
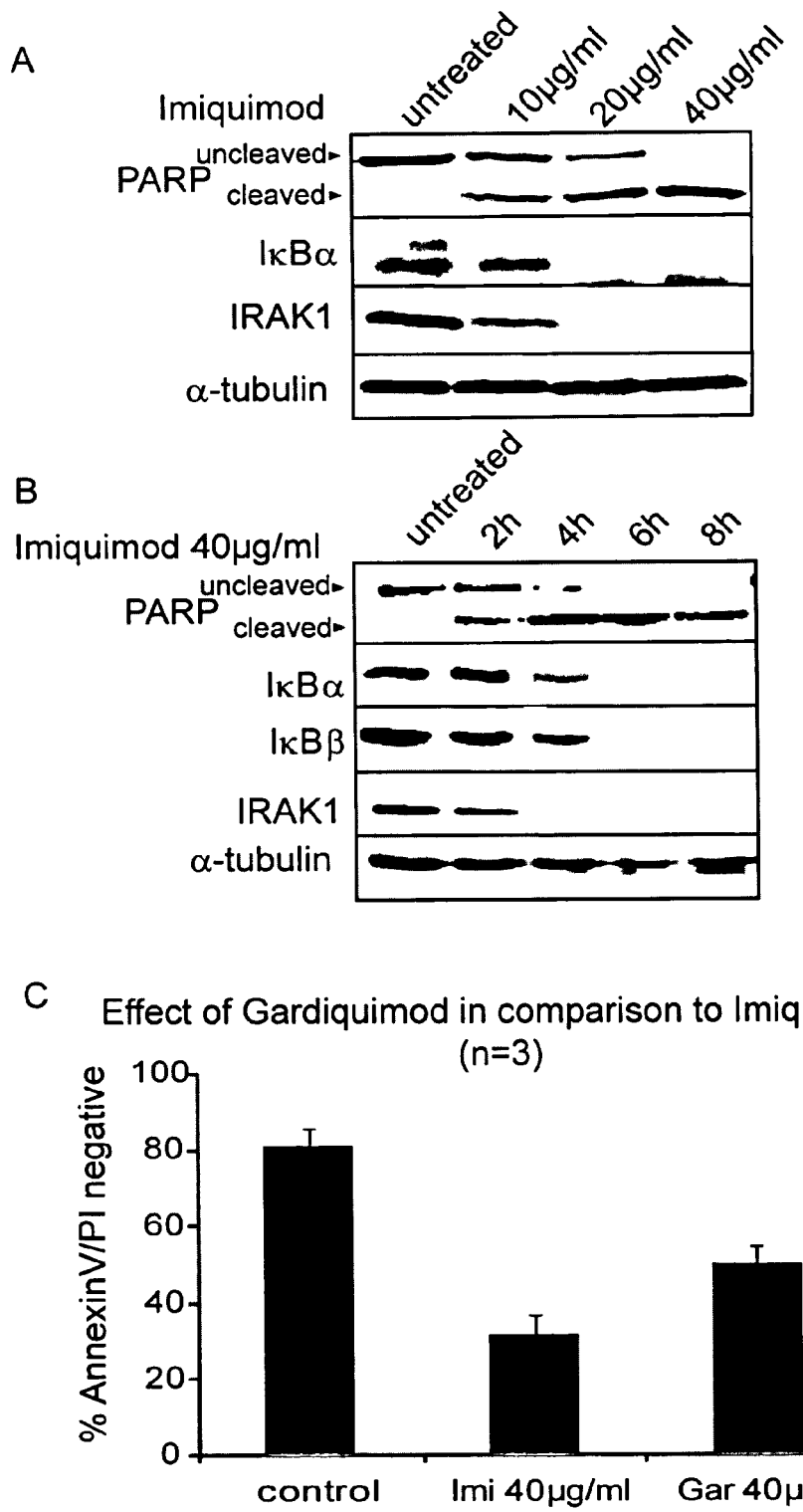

This application is the U.S. National Phase of PCT/EP2009/003736, filed May 26, 2009, which claims priority from European Patent Application No.: EP 08009559.9, filed May 26, 2008, all of which are incorporated herein by reference in entirety.

The present invention relates to the medical and pharmaceutical use of substituted 1H-imidazo[4,5-c]quinolin-4-amines, in particular Imiquimod® and Gardiquimod®, alone or preferably in combination with Akt inhibitors, in particular with Akti1/2 and AktX, and most preferably with Akti1/2, in the treatment, prevention and/or amelioration of haematological cancers, in particular myeloma disorders or B-cell disorders, and most particular in the therapy of multiple myeloma.

Multiple myeloma (MM) is a B-cell malignancy of terminally differentiated plasma cells distributed within the bone marrow. It is the second most common haematological malignancy and the most common cancer interfering with bone metabolism with up to 90% of patients developing bone lesions, a hallmark of MM. The mechanism of tumor development is most likely a multistep transformation which includes genetic alterations, alterations of the bone marrow microenvironment and a dysfunction of the immune system[1]. The annual incidence of MM in Europe and United States is 3-4 per 100.000[2]. The median age of patients diagnosed with MM is 65; the median survival ranges from three to four years. Despite the dramatic increase in therapeutic options for MM in the last 40 years, the disease is still incurable. Present therapies separate between patients which are candidates for autologous stem cell transplantation (age <65, good physical condition), and those that shall be treated solely by a conventional or high-dose chemotherapeutic approach[3]. In any case, chemotherapeutic agents are applied which, besides being unable to cure MM, are associated with relevant side effects because of their low specificity. Consequently, novel biological therapies that, alone or in combination with available therapeutics, specifically target myeloma cells are essential for efficient strategies in myeloma therapy.

Accordingly, the problem underlying the present invention is the provision of means and methods for the treatment as well as the potential prevention of haematological cancer disorders, in particular in multiple myeloma.

This technical problem is solved by the embodiments provided herein and as characterized in the claims. Specifically and in accordance to the present invention, a solution to this technical problem is achieved by providing the use of a compound of the following formula I

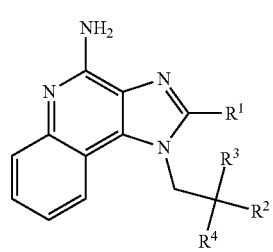

(formula I)

wherein
$R^1$ is H or —$CH_2$—$NR^5$—$(CH_2)_m$—$CH_3$, whereby m is an integer of 0 to 3 and $R_5$ is H or $C_1$-$C_4$ alkyl; and
$R^2$, $R^3$, $R^4$ are independently selected from H, $C_1$-$C_4$ alkyl, OH, $NH_2$, CN, Cl, Br, I or F, or a pharmaceutically acceptable salt, derivative or prodrug thereof in combination with an Akt inhibitor
for the preparation of a pharmaceutical composition for the treatment, prevention and/or amelioration of a haematological cancer, in particular multiple myeloma.

In a further embodiment, it is also envisaged to use a compound of the following formula I

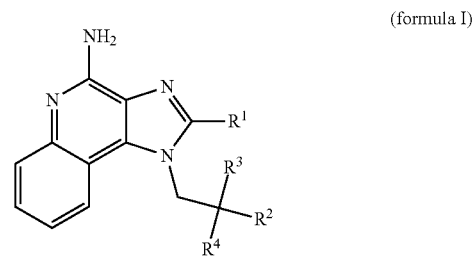

(formula I)

wherein
$R^1$ is H or —$CH_2$—$NR^5$—$(CH_2)_m$—$CH_3$, whereby m is an integer of 0 to 3 and $R_5$ is H or $C_1$-$C_4$ alkyl; and
$R^2$, $R^3$, $R^4$ are independently selected from H, $C_1$-$C_4$ alkyl, OH, $NH_2$, CN, Cl, Br, I or F, or a pharmaceutically acceptable salt, derivative or prodrug thereof for the preparation of a pharmaceutical composition for the treatment, prevention and/or amelioration of a haematological cancer, in particular multiple myeloma In a preferred embodiment, of this invention, the compound to be employed in the medical/pharmaceutical intervention of a haematological cancer/haematological disorder in combination with an Akt inhibitor is a compound as defined as formula I, wherein two of said $R^2$-$R^4$ are $C_1$-$C_4$ alkyl and the remaining is H. Particularly preferred in this context a compound of formula I as defined herein wherein said $R^1$ is H. In such a particular preferred embodiment of this invention, said compound has the following formula II:

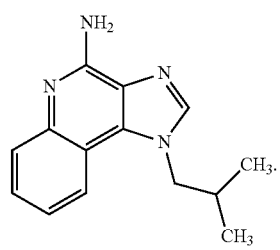

(Imiquimod®)

The present invention also relates to the compound to be employed in the medical/pharmaceutical intervention of a haematological cancer/haematological disorder in combination with an Akt inhibitor is a compound as defined as formula I herein above and wherein two of $R^2$-$R^4$ are $C_1$-$C_4$ alkyl and the remaining is OH. In accordance with this embodiment of this invention, said $R^1$ is —$CH_2$—NH—$C_2H_5$. Most preferably, in context of this embodiment of the present invention, the compound to be employed in the medical/pharmaceutical intervention of a haematological cancer, in particular in the treatment, prevention and/or amelioration of a B-cell disorder, more particular multiple myeloma, has the following formula III:

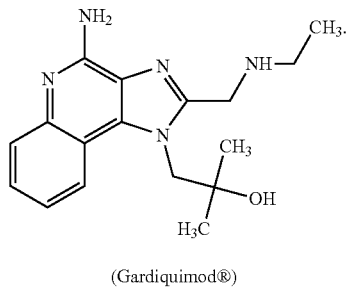 [SMILES: CCNCc1nc2c(N)nc3ccccc3c2n1CC(C)(C)O]

(Gardiquimod®)

Therefore, the present invention provides for the surprising finding, that imidazoquinolin derivates/compounds, like Imiquimod® and Gardiquimod® in combination with Akt inhibitors can be employed in a therapeutic method for the treatment of haematological cancers, in a particular in the treatment of multiple myeloma. Accordingly, the present invention describes in particular the use of Imiquimod® and Gardiquimod® (or pharmaceutically acceptable salts, prodrugs and derivatives of these compounds) in the treatment, prevention and or amelioration of blood cell disorders, in particular cancers, like multiple myeloma.

The family of Toll-like Receptors (TLRs), consisting of at least 10 highly conserved members, is involved in innate immune response by recognising conserved pathogenic structures like Lipopolysaccharide (TLR4), Flagellin (TLR5) or single stranded RNAs (TLR7)[4,5,6]. Upon binding of their target structure TLRs activate a NF-κB-dependent signalling pathway leading to secretion of type I interferons, interleukin-12 and other pro-inflammatory cytokines to induce immune defense in the infected organism[4].

Imiquimod® (R837 or 526308; 1-(2-methylpropyl)-1H-imidazo[4,5-c]quinolin-4-amine) is a nucleoside analogue and member of the imidazoquinoline family[7]. Interferon-inducing capability has been shown[8] and, with rather limited success, Imiquimod has also been tested as systemically applied anti-tumoral agent in mice[9] and humans[10]. Schon et al.[7,38,39] have observed weak apoptosis induction with Imiquimod® in cancer cells (melanoma, squamous cell carcinoma). Reduction in cell number by Imiquimod® has been shown in squamous cell carcinoma and melanoma cell lines at concentration of 50 µg/ml[38,39]. A weak apoptosis induction has been demonstrated in these cells after 24 h incubation with an Imiquimod® concentration of 50 µg/ml and 17.3% of the squamous cell carcinoma cells[38] and 15.8% of the melanoma cells[39] were apoptotic. Only after TLR7 was discovered[11], subsequent experiments showed that the induction of an immune response by Imiquimod® was due to TLR7 activation[12]. Currently, Imiquimod® is used as topical formulation (Aldara® 5% cream) for the treatment of viral lesions (HPV papillomas; condyloma) and malignant tumors of the skin[7], in particular in the treatment of actinic keratosis and superficial basal cell carcinoma.

In contrast, as presented in the appended examples, it was in the context of the present invention surprisingly found that apoptosis induction of multiple myeloma cells was measured after 24 h at a concentration of 10 µg/ml Imiquimod®. In a PARP cleavage assay, up to 100% apoptosis induction of multiple myeloma cells was measured at a concentration of 40 µg/ml Imiquimod®. and 70% in an AnnexinV/PI FACS analysis assay. Furthermore, an onset of apoptosis induction of multiple myeloma cells was shown after 2 h. 6 h to 8 h after Imiquimod® application (40 µg/ml) 100% apoptosis induction was shown in a PARP cleavage assay. As presented in the appended examples, it was also surprisingly found that Imiquimod® specifically induces apoptosis in multiple myeloma cells whereas other cells remain untargeted. Thus, it was in the context of the present invention surprisingly found that the human epidermoid carcinoma cell line A431 showed no significant apoptosis induction to Imiquimod®. Other cell lines tested (MDA468 (mammary gland adenocarcinoma), CHO (Chinese hamster ovary), ONK2 (human osteosarcoma), MCF7 (human breast cancer), HeLa (human cervix carcinoma), Raji, Daudi, Ramos (B-cell leukemia), C7H2 and Jurkat (T-cell leukemia)) also displayed no sensitivity to Imiquimod®.

Gardiquimod® is another imidazoquinoline compound useful in context of the present invention and is 1-(4-Amino-2-ethylaminomethylimidazo[4,5-c]quinolin-1-yl)-2-methyl-propan-2-ol; see also formula III provided herein above.

As documented in the appended example, it was surprisingly found in context of this invention that Imiquimod® and Gardiquimod® are very potent inhibitors of growth of multiple myeloma cells and that in particular co-therapeutic approaches/combination therapeutic approaches in the medical intervention in haematological cancers, preferably multiple myeloma(s) are surprisingly effective. The data provided in the appended example demonstrate that Imiquimod® potently and selectively induces apoptosis in multiple myeloma cell lines as well as malignant cells derived from multiple myeloma patient's, suggesting that this is independent of the interferon-inducing capability. Therefore, Imiquimod® (as well as Gardiquimod®) is indentified herein as potent inducer of apoptosis in multiple myeloma cell lines as well as malignant cells derived from multiple myeloma patient's. Data provided in the appended examples document that in particular Imiquimod® is a potent drug in the treatment of multiple myeloma.

Furthermore, the appended examples illustrate in a non-limiting way that the herein defined imidazoquinoline compounds, in particular Imiquimod® and Gardiquimod®, and most preferably Imiquimod® can be used in co-therapy/combination therapy approaches in the treatment of haematological cancers, in particular in the treatment of multiple myeloma(s). Such a co-therapy/combination therapy may comprise the compounds and drugs, like Thalidomide, Dexamethasone®, Melphalan, Sorafenib or PKC inhibitors (like Gö6976).

In particular in the herein defined co-therapy/combination therapy approaches, it is envisaged that the herein defined imidazoquinoline compounds, in particular Imiquimod® and Gardiquimod®, and most preferably Imiquimod®, are administered to a subject in need of treatment and/or prevention of the herein defined haematological disorders/cancer, in combination with the above described additional drugs. These drugs may be given to the subject before, during or after the treatment with the herein defined imidazoquinoline compounds, in particular Imiquimod® and Gardiquimod®, and most preferably Imiquimod®.

As further documented in the appended examples, it was surprisingly found that Imiquimod® and Gardiquimod® in combination with Akt inhibitors, like Triciribine, Perifosine, GSK690693, Akti1/2 and AktX, very potently and specifically induce apoptosis in multiple myeloma cell lines, whereas other cells remain untargeted. Thus, in particular co-therapeutic approaches/combination therapeutic approaches in the medical intervention in haematological cancers, preferably multiple myeloma(s) are surprisingly effective. Therefore, Imiquimod® (as well as Gardiquimod®) in combination with Akt inhibitors are indentified herein as potent super-additive inducers of apoptosis in multiple myeloma cell lines as well as malignant cells derived from multiple myeloma patients.

In particular, simultaneous application of the Akt inhibitors Akti1/2 or AktX and Imiquimod® had an outstanding super-additive apoptosis inducing effect. In context of the present invention, the term "super-additive" refers to an effect that creates an outcome that is more than additive compared to the outcome of the sum of the individual effects. Thus, this term refers to the surprisingly found outstanding enhancing apoptosis effect of both, Akt inhibitors (in particular Triciribine, Perifosine, GSK690693, more preferably AktX and most preferably Akti1/2) and imidazoquinoline compounds (in particular Imiquimod® and Gardiquimod®, and most preferably Imiquimod®), whereas the outstanding effect of Akt inhibitors and the imidazoquinoline compounds induces much more apoptosis than the sum of their individual effects. Thus, "super-additive" is to be understood as the result of the effect when the Akt inhibitors (in particular Triciribine, Perifosine, GSK690693, more preferably AktX and most preferably Akti1/2) and imidazoquinoline compounds work in concert together to create an apoptosis induction value that is much more compared to the sum of their individual apoptosis induction values. Therefore, a "super-additive" effect takes place when the interaction of the two agents results in an effect that is greater than the sum of their individual effects. In this context, the present invention provides for the surprising finding that the simultaneous application of Imiquimod® in combination with Akt inhibitors, like Akti1/2 and AktX, displays an outstanding super-additive apoptosis enhancing effect on multiple myeloma cells. This "super-additive" effect is documented in the appended examples, wherein Imiquimod® alone, as well as Akti1/2 alone induced some apoptosis and displayed only mild effects at the doses used. However, in combination, the effect was outstanding, wherein said effect was by far more than the sum of their individual effects. As further demonstrated in the examples, the super-additive effect is the result of different apoptosis inducing effects by the individual interaction of Akt inhibitors and imidazoquinoline compounds with distinct cellular pathways. As outlined above, Imiquimod® interacts and activates the TLR7 pathway, whereas the Akt inhibitors inhibit the Akt-pathway, thus inhibiting the cellular survival pathway mediated by Akt.

The data provided in the appended examples document that in particular Imiquimod® in combination with Akt inhibitors is a potent drug in the treatment of multiple myeloma. Such a co-therapy/combination therapy preferably comprises the Akt inhibitors Triciribine, Perifosine and GSK690693 and most preferably Akti1/2 or AktX.

The Akt protein family, which members are also called protein kinases B (PKB), plays an important role in mammalian cellular signalling. In humans, there are three genes in the "Akt family": Akt1, Akt2, and Akt3. These genes code for enzymes that are members of the serine/threonine-specific protein kinase family (EC 2.7.11.1). Akt1 is involved in cellular survival pathways, by inhibiting apoptotic processes. Akt1 is also able to induce protein synthesis pathways, and is therefore a key signaling protein in the cellular pathways that lead to skeletal muscle hypertrophy, and general tissue growth. Since it can block apoptosis, and thereby promote cell survival, Akt1 has been implicated as a major factor in many types of cancer[33]. Akt2 is an important signaling molecule in the Insulin signaling pathway. It is required to induce glucose transport[34]. The role of Akt3 is less clear, though it appears to be predominantly expressed in brain. It has been reported that mice lacking Akt3 have small brains[35]. Akt possesses a protein domain known as PH domain, or Pleckstrin Homology domain, named after Pleckstrin, the protein in which it was first discovered. This domain binds to phosphoinositides with high affinity. Akt regulates cellular survival[40] and metabolism by binding many downstream effectors, e.g. Nuclear Factor-KB, Bcl-2 family proteins and murine double minute 2 (MDM2).

Akt inhibitors are used to block the activation of Akt or the progression of the signal from Akt to the substrate. This can be achieved by blocking the proper localisation of Akt like in Akti-1/2 or Perifosine or via ATP analogues which block phosphorylation (Triciribine). The molecular mechanisms how some other inhibitors work are not investigated in detail.

Currently, no Akt inhibitor is known to be used in clinical applications. However, at present, several Akt inhibitors are clinically tested in clinical phase I or II trials[37], i.e. Triciribine (Vioquest), GSK690693 (Glaxo Smith Kline), and Perifosine (Keryx Pharmaceuticals). The molecular mechanism of Triciribine is not known in detail, however, it has been found that Triciribine avoids the phosphorylation of Akt. Currently, Triciribine is tested in clinical phase I for "adult patients with advanced hematologic malignancies" and in phase I for "adult subjects with metastatic cancer". GSK690693 has been tested in clinical phase I for "subjects with relapsed or refractory hematologic malignancies" and in phase I for "investigate the safety, tolerability, PK, and pharmacodynamics". However, both studies have been withdrawn and terminated because due to hyperglycaemia. For Perifosine, at present, there are 36 clinical phase I and II studies alone or in combination with other substances (http://clinicaltrials.gov/ct2/results?term=perifosine&pg=1).

Akti1/2 is an Akt inhibitor that can be used in co-therapy/combination therapy approaches in the treatment of haematological cancers, in particular in the treatment of multiple myeloma and is 1,3-Dihydro-1-(1-((4-(6-phenyl-1H-imidazo[4,5-g]quinoxalin-7-yl)phenyl)methyl)-4-piperidinyl)-2H-benzimidazol-2-one; see also the following formula IV:

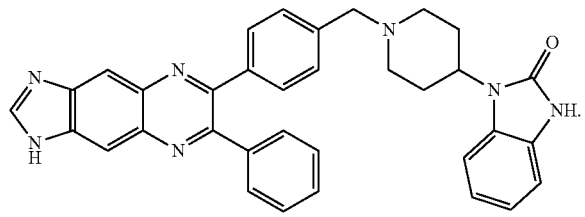

(Akti1/2 inhibitor)

Akti1/2 is also known under the alternative name Akt Inhibitor VIII, is soluble in DMSO, has the molecular formula $C_{34}H_{29}N_7O$ and has a molecular weight of 551.6. Akti1/2 is a cell-permeable, potent, and selective inhibitor of Akt1/Akt2/Akt3 activity ($IC_{50}$=58 nM, 210 nM, and 2.12 µM for Akt1, Akt2, and Akt3, respectively, in in vitro kinase assays). The inhibition is reported to be pleckstrin homology (PH) domain-dependent. It does not exhibit any inhibitory effect against PH domain-lacking Akts, or other closely related AGC family kinases, PKA, PKC, and SGK, even at concentrations as high as 50 µM. It overcomes Akt1/Akt2-mediated resistance to chemotherapeutics in tumor cells and is shown to block basal and stimulated phosphorylation/activation of Akt1/Akt2 both in cultured in vitro and in vivo mice.[26, 27, 28, 29, 30, 31]

AktX is an Akt inhibitor that can be used in co-therapy/combination therapy approaches in the treatment of haematological cancers, in particular in the treatment of multiple myeloma and is a 10-(4'-(N-diethylamino)butyl)-2-chlorophenoxazine, HCl; see also the following formula V:

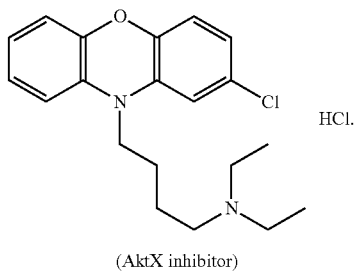

(AktX inhibitor)

AktX is also known under the alternative name Akt Inhibitor X, is soluble in $H_2O$, has the molecular formula $C_{20}H_{25}ClN_2 \cdot HCl$ and has a molecular weight of 381.4. AktX is a cell-permeable and selective inhibitor of the phosphorylation of Akt and its in vitro kinase activity (complete inhibition <5 μM) with minimal effect on PI 3-K, PDK1, or SGK1. It is shown to suppress growth of Rh (rhabdomyosarcoma) cell lines ($IC_{50}$=2-5 μM), inhibit IGF-I-stimulated nuclear translocation of Akt, and prevent phosphorylation of the downstream targets, mTOR, p70S6 kinase, and S6 ribosomal protein. Unlike Akti1/2, the mode of inhibition is not PH domain-dependent.[32].

Therefore, the present invention provides for the surprising finding, that imidazoquinolin derivates/compounds, like Imiquimod® and Gardiquimod®, in combination with Akt inhibitors, like Akti1/2 and AktX, displayed favourable super-additive combination effects. In particular, simultaneous application of the Akt inhibitors Akti1/2 or AktX and Imiquimod® had an outstanding super-additive apoptosis inducing and a strong combinatory anti-tumoral effect on multiple myeloma cells. Thus, that imidazoquinolin derivates/compounds, like Imiquimod® and Gardiquimod®, in combination with Akt inhibitors, preferably with Triciribine, Perifosine and GSK690693, more preferably with Akti1/2 and AktX, and most preferably with Akti1/2, can be employed in therapeutic methods, combination therapeutic approaches/co-therapeutic approaches for the treatment of multiple myeloma. Accordingly, the present invention describes in particular the use of Imiquimod® and Gardiquimod® (or pharmaceutically acceptable salts, prodrugs and derivatives of these compounds) in combination with Akt inhibitors, preferably with Triciribine, Perifosine and GSK690693, more preferably with Akti1/2 and AktX, and most preferably with Akti1/2 (or pharmaceutically acceptable salts, prodrugs and derivatives of these compounds), in the treatment, prevention and or amelioration of blood cell disorders, in particular cancers, like multiple myeloma.

It is also envisaged that the imidazoquinoline compounds, in particular Imiquimod® and Gardiquimod®, and most preferably Imiquimod® described herein alone or preferably in combination with the Akt inhibitors Triciribine, Perifosine and GSK690693, more preferably with Akti1/2 and AktX, and most preferably with Akti1/2, may be administered to a subject as compounds per se in their use as pharmacophores or pharmaceutical compositions or may be formulated as medicaments. The pharmaceutical compositions may optionally comprise pharmaceutically acceptable excipients, such as carriers, diluents, fillers, desintegrants, lubricating agents, binders, colorants, pigments, stabilizers, preservatives or antioxidants.

The pharmaceutical compositions can be formulated by techniques known to the person skilled in the art, such as the techniques published in Remington's Pharmaceutical Sciences, 20th Edition. The pharmaceutical compositions can be formulated as dosage forms for, e.g. oral administration. However, also parenteral, such as intramuscular, intravenous, subcutaneous, intradermal, intraarterial, rectal, nasal, topical or vaginal administration is envisaged. In context of the present invention, the most preferred route of administration of the herein defined imidazoquinoline compounds, in particular Imiquimod® and Gardiquimod®, and most preferably Imiquimod® alone or preferably in combination with Akt inhibitors, preferably with the Akt inhibitors Triciribine, Perifosine and GSK690693, more preferably with Akti1/2 and AktX, and most preferably with Akti1/2, is oral administration.

Dosage forms for oral administration include coated and uncoated tablets, soft gelatine capsules, hard gelatine capsules, lozenges, troches, solutions, emulsions, suspensions, syrups, elixiers, powders and granules for reconstitution, dispersible powders and granules, medicated gums, chewing tablets and effervescent tablets.

Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler.

Pharmaceutically acceptable salts of compounds that can be used in the present invention can be formed with various organic and inorganic acids and bases. Exemplary acid addition salts comprise acetate, adipate, alginate, ascorbate, benzoate, benzenesulfonate, hydrogensulfate, borate, butyrate, citrate, caphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pectinate, persulfate, 3-phenylsulfonate, phosphate, picate, pivalate, propionate, salicylate, sulfate, sulfonate, tartrate, thiocyanate, toluenesulfonate, such as tosylate, undecanoate and the like. Exemplary base addition salts comprise ammonium salts, alkali metall salts, such as sodium, lithium and potassium salts; earth alkali metall salts, such as calcium and magnesium salts; salts with organic bases (such as organic amines), such as benzazethine, dicyclohexylamine, hydrabine, N-methyl-D-glucamine, N-methyl-D-glucamide, t-butylamine, salts with amino acids, such as arginine, lysine and the like.

Pharmaceutically acceptable solvates of compounds that can be used in the present invention may exist in the form of solvates with water, for example hydrates, or with organic solvents such as methanol, ethanol or acetonitrile, i.e. as a methanolate, ethanolate or acetonitrilate, respectively.

Pharmaceutically acceptable prodrugs of compounds that can be used in the present invention are derivatives which have chemically or metabolically cleavable groups and become, by solvolysis or under physiological conditions, the compounds of the invention which are pharmaceutically active in vivo. Prodrugs of compounds that can be used in the present invention may be formed in a conventional manner with a functional group of the compounds such as with an amino or hydroxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985).

These pharmaceutical compositions described herein can be administered to the subject at a suitable dose. The dosage regiment will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Generally, the regimen as a regular administration of the pharmaceutical composition comprising the herein defined should be in the range of 0.1 µg to 5000 mg units per day, in some embodiments 0.1 µg to 1000 mg units per day. If the regimen is a continuous infusion, it may also be in the range of 0.1 ng to 10 µg units per kilogram of body weight per minute, respectively. Progress can be monitored by periodic assessment. It is also envisaged to use regimens which provide for escalating doses. It is in particular preferred that the patient in need of the medical intervention as provided herein receives high dosages of the herein defined imidazoquinoline compounds, in particular Imiquimod®. Such high dosages may comprise between 1 to 500 mg/kg, however, also other dosage regimens are envisaged and can be attended to by the attending physician. There is further provided a regimen as a regular administration of the pharmaceutical composition comprising the herein defined imidazoquinoline compounds in combination with Akt inhibitors, preferably with the Akt inhibitors Triciribine, Perifosine and GSK690693, more preferably with Akti1/2 and AktX, and most preferably with Akti1/2, wherein said combined preparation is for simultaneous, separate or sequential use.

In the context of the present invention, the following modes of administration of the imidazoquinoline compounds, in particular Imiquimod® and Gardiquimod®, and most preferably Imiquimod® alone or preferably in combination with Akt inhibitors, preferably with the Akt inhibitors Triciribine, Perifosine and GSK690693, more preferably with Akti1/2 and AktX, and most preferably with Akti1/2, are preferred:

Oral administration in constant or escalating doses;
Subcutaneous administration in constant or escalating doses; and/or
Intravenous administration in constant or escalating doses.

Accordingly, the present invention provides for means and methods for the treatment of subjects in need of such a treatment (either curative or preventive) which suffer from haematological disorders/cancers, in particular multiple myeloma. The method of treatment of such disorder comprises the administration of a pharmaceutically active amount of a herein defined imidazoquinoline compounds, in particular Imiquimod® and Gardiquimod®, and most preferably Imiquimod® alone or preferably in combination with Akt inhibitors, preferably with the Akt inhibitors Triciribine, Perifosine and GSK690693, more preferably with Akti1/2 and AktX, and most preferably with Akti1/2. As also illustrated in the appended examples, such a method of treatment may also comprise the co-administration of additional compounds/medicaments and the herein described medical/pharmaceutical use of the herein defined imidazoquinoline compounds, in particular Imiquimod® and Gardiquimod®, and most preferably Imiquimod® is in particular envisaged in co-therapy approaches and combination therapy approaches. In particular, the method of treatment preferably comprises the co-administration and the herein described medical/pharmaceutical use of the herein defined imidazoquinoline compounds, in particular Imiquimod® and Gardiquimod®, and most preferably Imiquimod® in combination with Akt inhibitors, preferably with the Akt inhibitors Triciribine, Perifosine and GSK690693, more preferably with Akti1/2 and AktX, and most preferably with Akti1/2 and said co-therapy approaches and combination therapy approaches is in particular envisaged.

The subject to be treated or in need of treatment according to this invention is preferably a mammalian subject. Said subject is most preferably a human subject. In particular, the subject to be treated is a human patient that suffers from haematological disorders/cancers, and most preferably multiple myeloma.

The following figures show and illustrate the present invention:

FIG. 1: Apoptosis induction in OPM2 cells by TLR7 agonists: Apoptosis was assessed by analyses of PARP cleavage (uncleaved 116 kD, cleaved 89 kD) or Annexin V/PI staining. The activation of the TLR pathway is indicated by the degradation of IRAK1 (81 kD) IκB-α (39 kD) and IκB-β (48 kD)) (in case of B) in Western blots. α-tubulin serves as loading control (50 kD). A: Cells were treated for 16 h with different concentrations of Imiquimod® in full medium. B: Cells were treated for different time periods with 40 µg/ml Imiquimod® in full medium. C: The TLR7 agonists Imiquimod® (40 µg/ml) and Gardiquimod® (40 µg/ml) induce apoptosis in OPM2 cells in a comparable extend after 24 h incubation.

Figure 2:
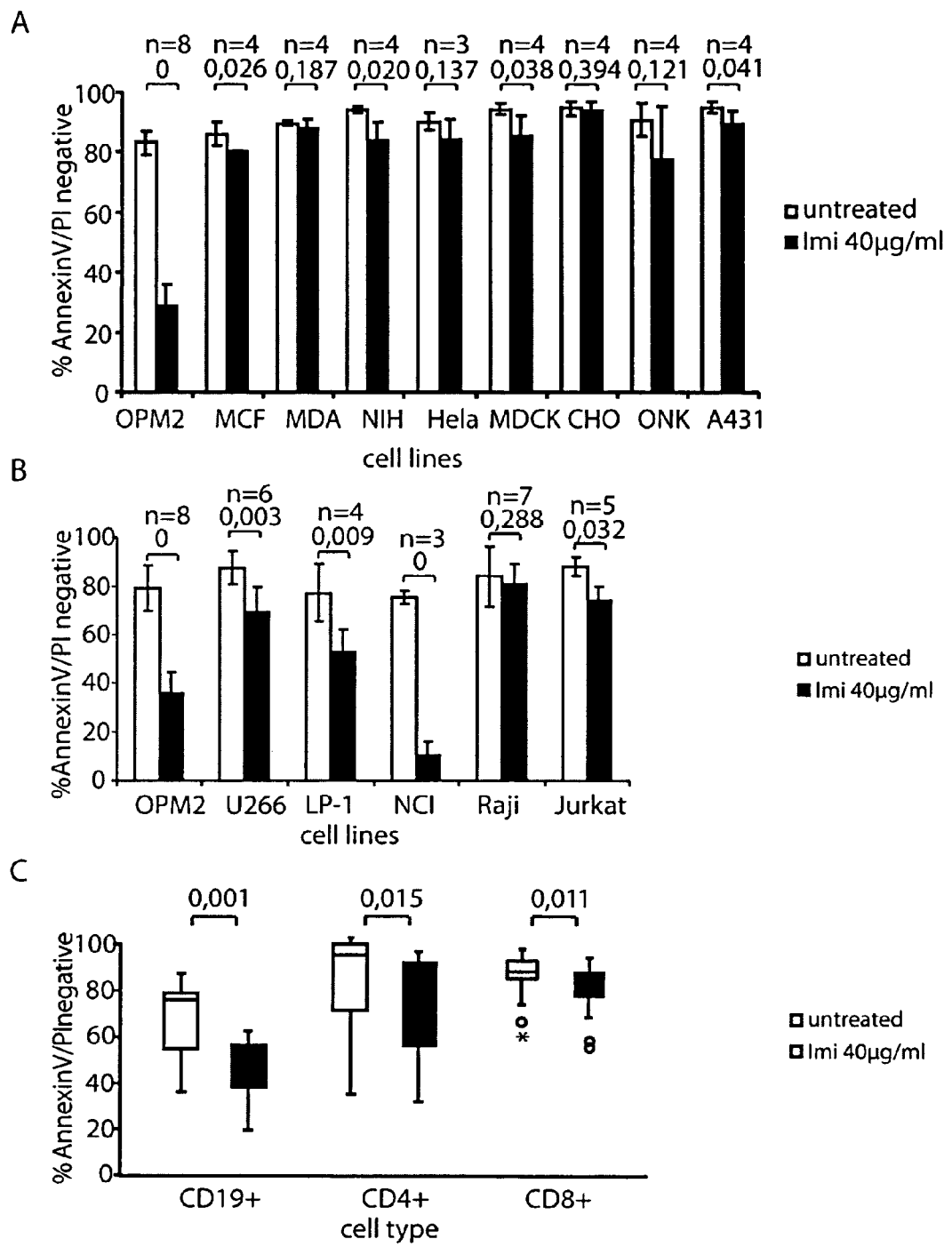

FIG. 2: The effect of Imiquimod® on different cell types/lines: Different cell lines were treated with 40 µg/ml Imiquimod® for 24 h and apoptosis induction was detected by Annexin V/PI staining. Means are displayed, error bars indicate standard deviation, paired t-test (A, B) or U-test (C) were performed and p-values are displayed below sample numbers (0 indicates p≦0.001) A: Adherent cell lines showed no significant or only little induction of apoptosis upon Imiquimod® treatment (OPM-2 cells are included for comparison). B: All multiple myeloma cell lines (U266, LP-1, OPM-2, NCI) were significantly, though to a different extent, sensitive to apoptosis induction by Imiquimod®. Raji were not significantly sensitive while Jurkat were mildly affected by Imiquimod®. C: CD4+ and Cd8+ T-cells from 12 healthy donors displayed low but significant sensitivity, CD 19+ cells were more sensitive.

Figure 3:
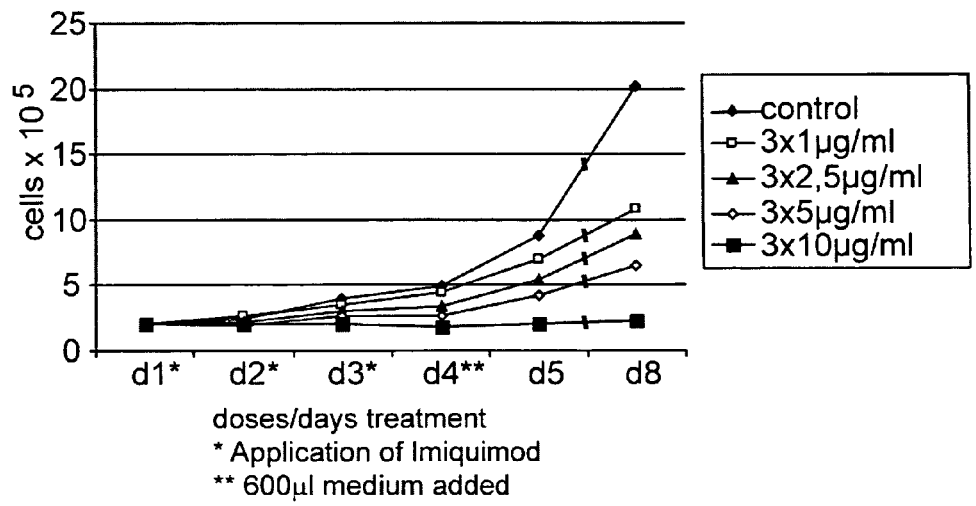

FIG. 3: Effect of multiple low doses of Imiquimod® on OPM2 cells: Cells were treated once a day throughout three days (d1-d3) with different doses of Imiquimod®. On fourth day medium was exchanged to remove Imiquimod® and ensure nutrition supply. Living and dead cells could not be distinguished with the technique used. Growth inhibition of Imiquimod® is concentration dependent.

Figure 4:
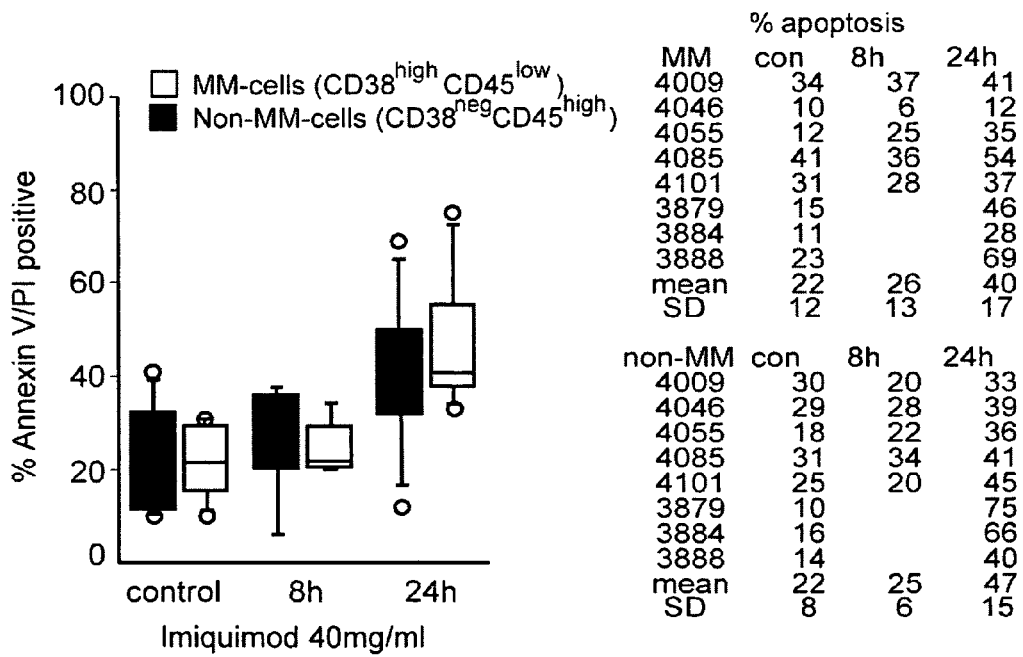

FIG. 4: Left panel: BMMCs from bone marrow aspirates of MM patients were left untreated or treated with Imiquimod® (40 µg/ml) for the indicated time periods. Subsequently, the percentage of apoptosis in the MM cell fraction ($CD38^{high}CD45^{low}$) and the non-tumor fraction ($CD38^{neg}CD45^{high}$) was detected by staining cells for 15 min with a mixture of Annexin-V-FITC, anti-CD38-PE and anti-CD45-PC-5 followed by flow cytometric analysis. Results are presented in a box-and-whisker diagram. Each box represents the central 50% of the data and the whiskers extend from the box to the $90^{th}$ percentile and the $10^{th}$ percentile of the data. All observations <$10^{th}$ or > the $90^{th}$ percentile are presented as circles.

Right panel: The percentages of spontaneous apoptosis (con) or Imiquimod®-induced apoptosis at different time points (8 h, 24 h) in MM cells (upper panel) or non-MM cells (lower panel) in individual samples from MM patients are given.

Figure 5:
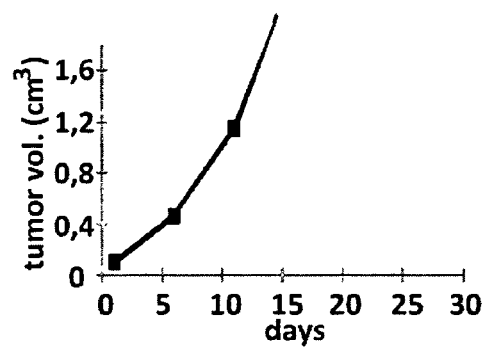
Figure 5:
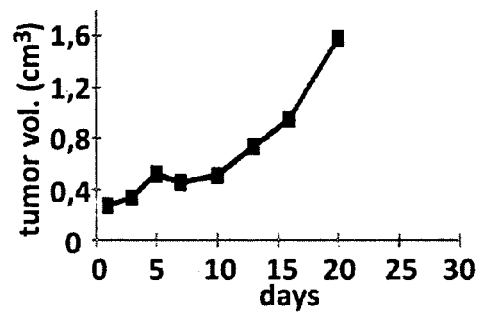
Figure 5:
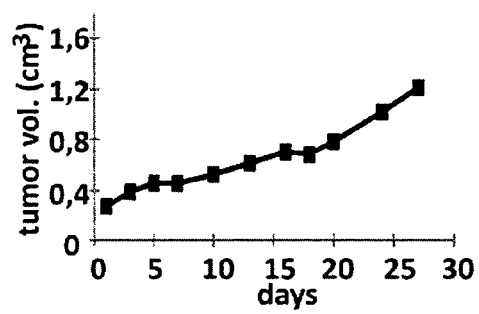
Figure 5:
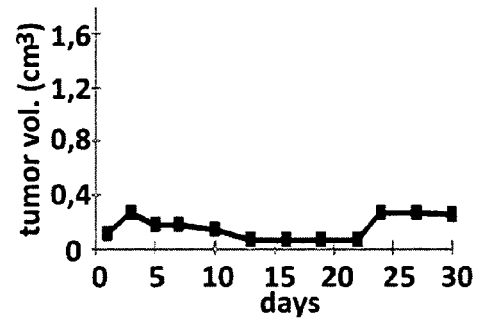
Figure 5:
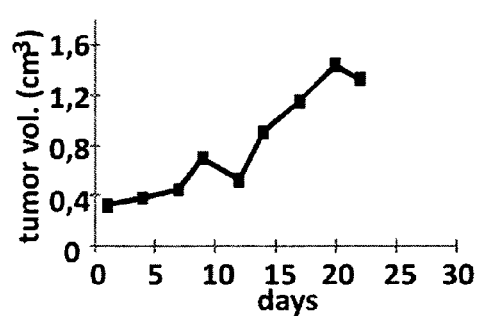
Figure 5:
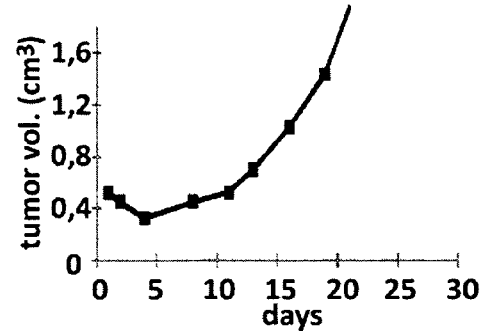

FIG. 5: Effect of Imiquimod® on tumor growth in vivo: A: Tumor growth in mice treated with vehicle. Results of two representative mice are presented. B: Tumor volume in mice treated with 10 mg/kg Imiquimod® s.c. twice daily. Results of four representative mice are presented.

Figure 6:
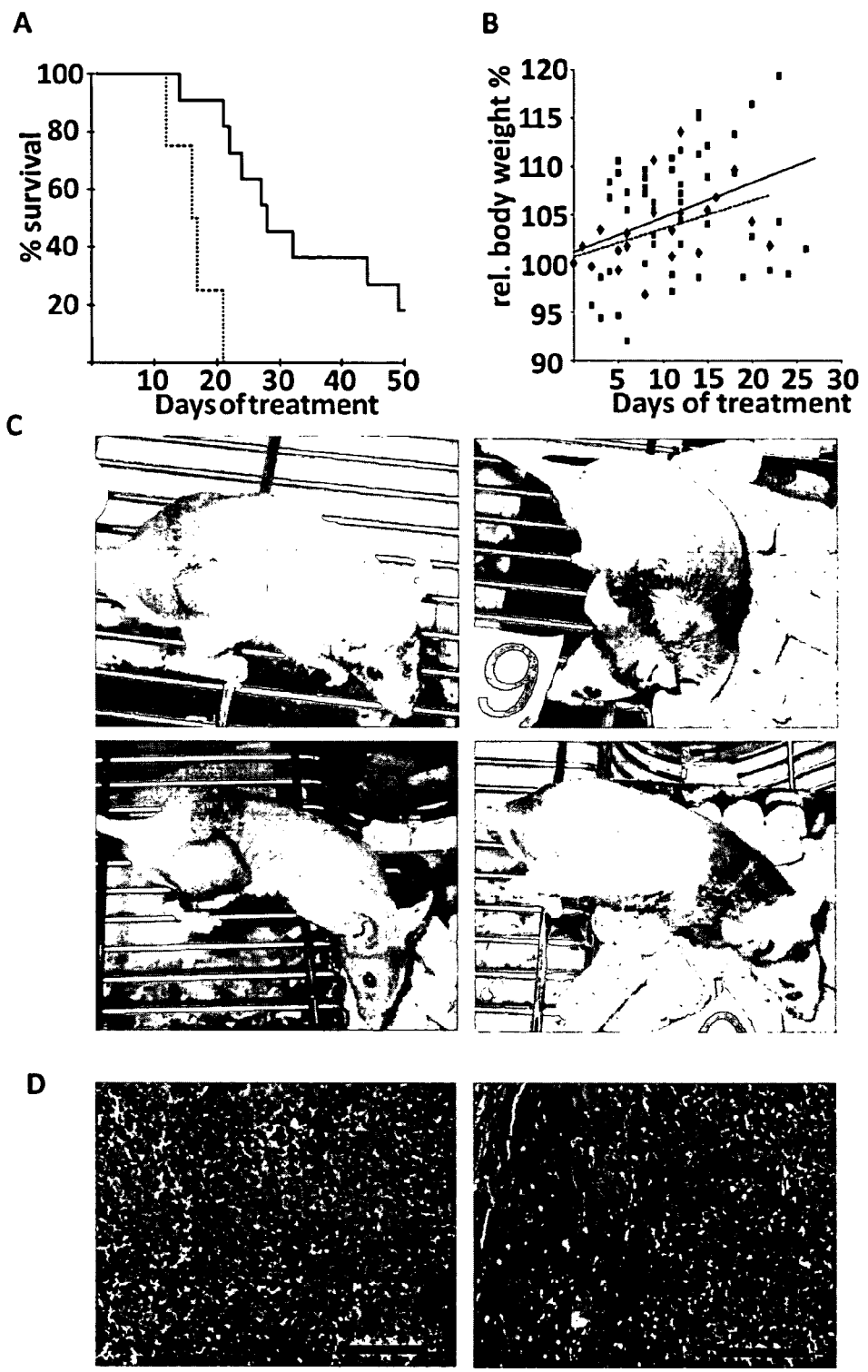

FIG. 6: In vivo effect of Imiquimod®: A: Mice with multiple myeloma-xenografts were treated with 10 mg/kg Imiquimod® (——) or H$_2$O (———) until the average tumor diameter reached 1.5 cm and then sacrificed. Survival was evaluated from first day of treatment until death. B: Relative body weight development from mice treated with Imiquimod® (indicated as black quadrat, ——) or water (indicated as black diamond, - - - ). C: Tumor development from day 1 (upper) to day 19 (lower) in a control (left) and a 10 mg/kg Imiquimod® treated (right) mouse; D: Hematoxolin and Eosine staining of representative areas of tumors of untreated (left) and treated (right) mice. The size bar indicates 100 µm.

Figure 7:
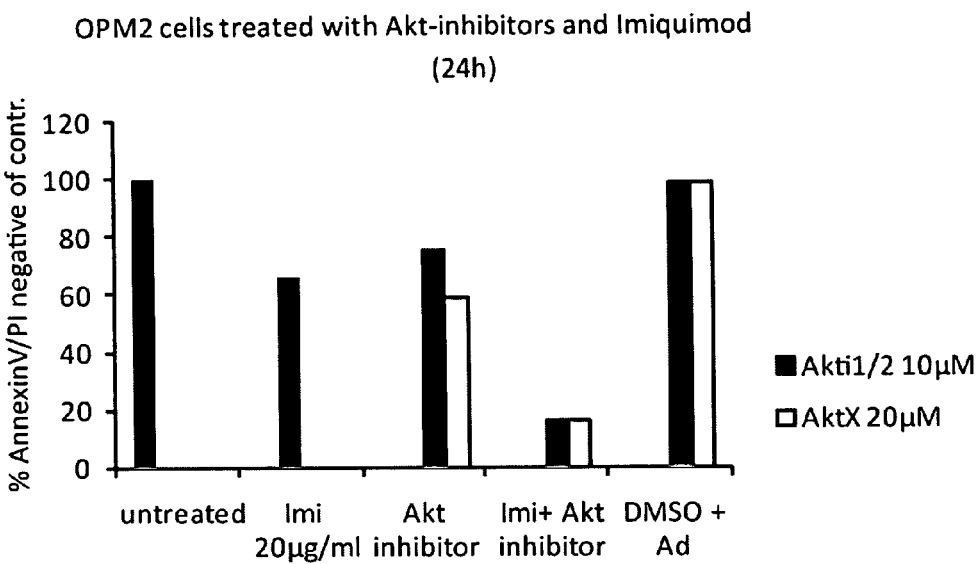
Figure 7:
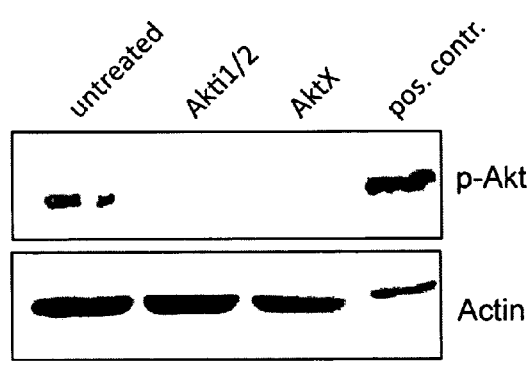

FIG. 7: The effect of different Akt inhibitors alone and in combination with Imiquimod® on OPM2 cells. A: OPM2 cells were left untreated, treated with 20 µg/ml Imiquimod® alone, with the indicated amounts of Akt inhibitors alone, or in combination with Imiquimod®. Apoptosis induction was measured after 24 h by AnnexinV/PI FACS analysis. Corresponding amounts of the solvents of the compounds, H$_2$O (Imiquimod®) and DMSO (Akt-inhibitors) were used as controls. B: The effect of Akt inhibitors on Akt phosphorylation was measured by Western blot with phospho-Akt antibody (60 kD, upper panel). Actin served as a loading control (45 kD).

Figure 8:
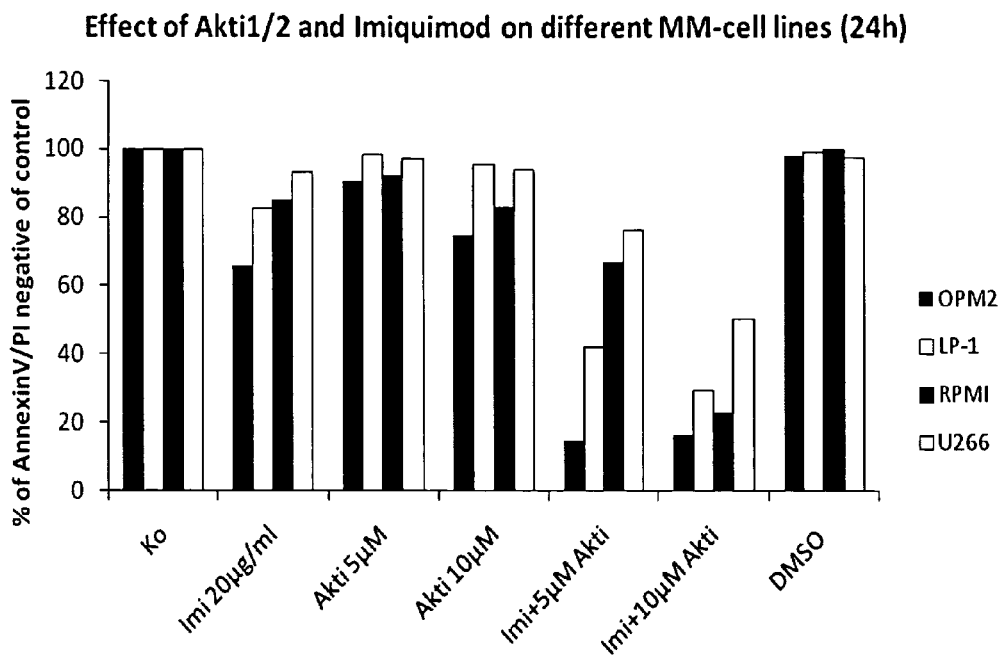

FIG. 8: The effect of Akti1/2 alone or in combination with Imiquimod® in different multiple myeloma cell lines. Cells were treated with 20 µg/ml Imiquimod®, 5 or 10 µM Akti1/2 or in combination of Imiquimod® and Akti1/2 at the named concentration: The order of the columns refer to the cell lines tested: OPM2, LP-1, RPMI, U266 (in each case, from left to right). DMSO was used as a control of the Akti1/2 solvent. Apoptosis induction was measured after 24 h by AnnexinV/PI FACS analysis.

Figure 9:
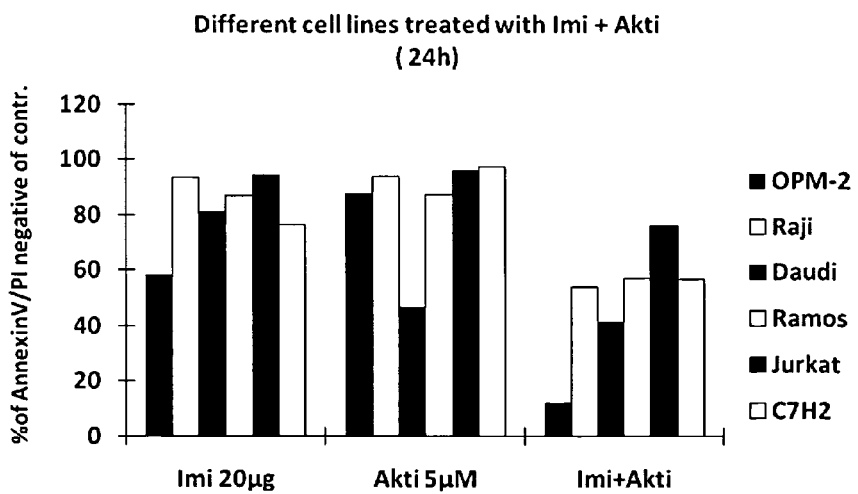

FIG. 9: The effect of Akti1/2 alone or in combination with Imiquimod® in different non-multiple myeloma cell lines. OPM2 cells (for comparison) and the Burkitt lymphoma cell lines Raji, Daudi and Ramos, and the T-ALL cell lines Jurkat and C7H2 were incubated with 20 µg/ml Imiquimod®, 5 µM Akti1/2 or both for 24 h and apoptosis was measured by AnnexinV/PI FACS analysis. The order of the columns refer to the cell lines tested: OPM2, Raji, Daudi, Ramos, Jurkat, C7H2 (in each case, from left to right).

Figure 10:
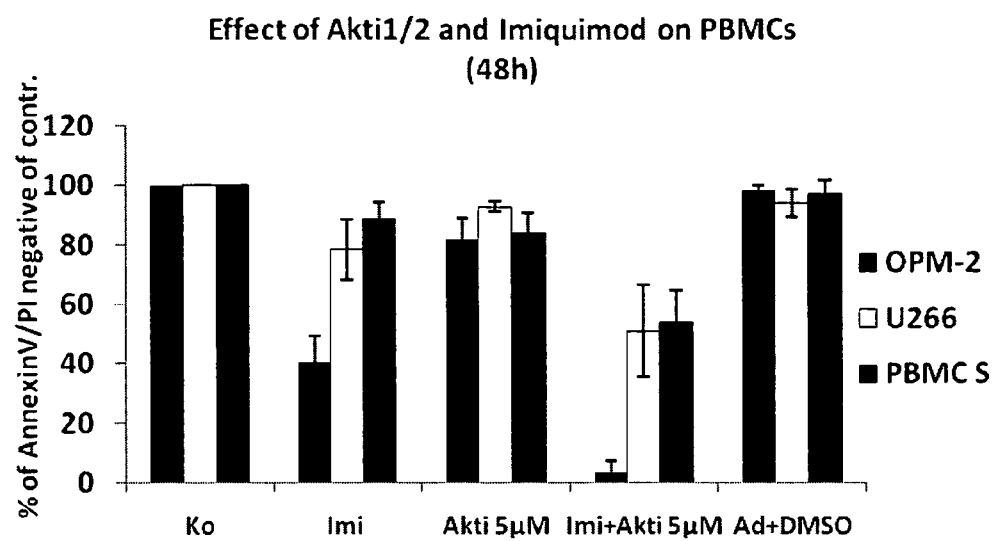

FIG. 10: The effect of Akti1/2 alone or in combination with Imiquimod® in peripheral blood mononuclear cells. OPM2 cells (for comparison) and PBMCs from healthy donors were incubated with 20 µg/ml Imiquimod®, 5 µM Akti1/2 or both for 48 h and apoptosis was measured by AnnexinV/PI FACS analysis. The order of the columns refer to the cell lines tested: OPM2, U266, PBMC S (in each case, from left to right).

The following non-limiting examples illustrate the invention:

EXAMPLE I

Materials and Methods as Employed in the Following

Cells and Culture Conditions:

Myeloma cell lines OPM-2, NCI-H929, LP1, RPMI-8226 and U266 were obtained from ATCC (American Type Culture Collection, Rockville Md., USA), and grown in RPMI-Medium 1640 (Life Technologies, Paisley, UK), L-glutamine 100 µg/ml (GIBCO, NY, USA), or RPMI 1640+GlutaMAX-I medium+25 mM HEPES (GIBCO, Paisley, U.K.) supplemented with 10% heat-inactivated fetal calf serum (PAA, Linz, Austria, or GIBCO, Paisley, U.K.), Penicillin (100 U/ml)-Streptomycin (100 µg/ml) (GIBCO, Paisley, U.K.). MDA468 and CHO cells (ATCC) were maintained in Dulbecco's Modified Eagle Medium (DMEM)/F-12+GltutaMAX-I medium (GIBCO, Paisley, U.K.) supplemented with 10% heat-inactivated fetal calf serum (GIBCO, Paisley, U.K.), Penicillin (100 U/ml)-Streptomycin (100 µg/ml) (GIBCO, Paisley, U.K.).

NIH3T3, ONK2, MCF7, A431, MDCK and HeLa (all ATCC) cells were maintained in high glucose DMEM (Applichem, Darmstadt, Germany) at pH 7.3, supplemented with 10% heat-inactivated fetal calf serum (GIBCO, Paisley, U.K.), Penicillin (100 U/ml)-Streptomycin (100 n/ml, GIBCO, Paisley, U.K.).

Raji, Ramos, Daudi and Jurkat cell lines were purchased from the German Collection of Microorganisms and Cell Culture (DSMZ; Braunschweig, Germany) and C7H2 cell line was obtained from R. Kofler[36]. Raji, Ramos, Daudi, C7H2 and Jurkat cell lines were cultured in RPMI-1640 Medium (Life Technologies, Paisley, UK) supplemented with 10% heat-inactivated fetal calf serum (PAA, Linz, Austria), L-glutamine 100 µg/ml (GIBCO, NY, USA), and Penicillin (100 U/nl)-Streptomycin (100 µg/ml, GIBCO, Paisley, UK). The supplemented media will further be called full media.

Adherent cells were trypsinized with 0.5% Trypsin (GIBCO, Paisley, UK) 1-10 minutes (depending on cell line) for passaging.

PBMCs were prepared using separation via Ficoll density gradient centrifugation (Biochrom AG, Berlin, Germany) according to the protocol of the manufacturer.

For collection of primary multiple myeloma cells, bone marrow aspirates from iliac crests were collected during routine examinations after obtaining informed patient consent. Clinical characteristics of patients are presented in Table 1. Bone marrow mononuclear cells (BMMCs) were separated by density centrifugation. Fresh blood samples were diluted 1:1 with RPMI 1640 medium and layered over Biocoll separating solution (1.077 g/ml, Biochrom AG, Berlin; blood/RPMI1640/Biocoll; 1:1:1, v/v/v). Centrifugation was carried out for 20 min at 400 g. The opaque layer on top of the Biocoll solution containing the multiple myeloma cells was collected, washed twice with PBS and resuspended in RPMI 1640 medium supplemented with 10% heat-inactivated fetal calf serum (both from PAA Laboratories, Linz, Austria) and 2 mmol/l L-glutamine (GIBCO, Grand Islands, N.Y., USA). The percentage of multiple myeloma cells within the BMMCs was determined by flow cytometry. Briefly, 2×10$^5$ cells were stained for 15 min with fluorochrome-labelled antibodies to CD38 (phycoerythrin, PE) and CD45 (phycoerythrin-cyanin 5, PC5) (both from Beckman Coulter Inc., Fullerton, Calif., USA), washed with PBS and were immediately analyzed using the FC500 flow cytometer and the RXP1.0 software (Beckman Coulter). MM cells were detected by their high expression of CD38 and weak to absent expression of CD45.

Chemicals and Antibodies:

Imiquimod® (tlrl-imq) and Gardiquimod® (tlrl-gdq) were ordered from Invivogen (San Diego, Calif., USA) and dissolved in sterile endotoxin-free water (supplied in the kid) to a stock of 5 mg/ml (Imiquimod®) or 1 mg/ml (Gardiquimod®). The NF-κB inhibitor BAY11-7082 (Calbiochem: La Jolla, Calif., USA) was dissolved in DMSO to a stock of 10 mM.

Rabbit anti IRAK1, PARP (recognizing PARP1), IκB-α and IκB-β antibodies was purchased from Cells Signaling Technology (Boston, Mass., USA). Mouse anti α-Tubulin was purchased from Sigma-Aldrich (Vienna, Austria). All antibodies used were diluted according to manufacturer's protocol.

Antibodies against human CD4, CD8, CD19 were obtained from BD-Pharmingen, San Diego, Calif., USA.

Akt inhibitors and antibodies: Akti1/2 (Cat. No.: 124018) and AktX (Cat. No.: 124020) were purchased from Calbiochem (Darmstadt, Germany). P-Akt antibody was purchased from Cell Signaling (#9271, Danvers, Mass., USA), actin antibody (pan Abs, clone ACTN05) from Labvision (#MS1295 P0, Thermo Fisher Scientific, Fremont, Calif., USA).

Annexin V/Propidium Iodide Apoptosis Assay:

After treatment adherent cells were trypsinized (as described before), and resuspended in corresponding full medium. Suspension cells or trypsinized adherent cells, supernatant and washing solution (1×PBS from washing before trypsinization) were pooled and then spun down (300 g for 3 min) washed in 2 ml and resuspended in 1000 of annexin V binding buffer and mixed with 2 µg/ml annexin V-Allophycocyanin (APC) (BD-Pharmingen, San Diego, Calif., USA) and 50 ng/ml of propidium iodide (PI; Sigma Aldrich). At least 10.000 cells were measured per sample using a Becton Dickinson FACSCalibur flow Cytometer (San Jose, Calif., USA). Percentage of Annexin V negative and PI negative cells were depicted in the figures. For the analysis of the pro-apoptotic activity of Imiquimod® in primary MM cells and non-malignant BMMCs, $5 \times 10^5$ cells BMMCs cells were treated with or without 40 µg/ml Imiquimod® for the indicated time periods. Cells were then harvested and washed twice with PBS. Detection of apoptotic cells was performed using the annexin V/PI assay according to manufacturers' instruction. Briefly, BMMCs were stained with a mixture of annexin V/FITC (Alexis Coorp., Laeufelfingen, Switzerland), propidium iodide (Sigma), anti-CD38-PE and anti-CD45-PC5 for 15 min at room temperature and immediately analyzed by flow cytometry. The percentages of viable cells (i.e. cells negative for annexin V/FITC and PI) within the MM ($CD38^{pos}CD45^{low/absent}$) and non-MM fraction ($CD38^{neg}/CD45^{pos}$) were determined by flow cytometry.

Western Blotting:

Cells were lysed in lysis-IP-Buffer supplemented with protease inhibitors and sodium orthovanadate. 10 µg of lysate were separated by SDS-PAGE (10% polyacrylamide) and transferred to methanol activated Hypond-P PVDF-membranes (Amersham, Freiburg, Germany) by semi-dry blotting. Membranes were blocked in a 3% bovine serum albumin solution or 5% non fat dry milk solution in phosphate buffered saline (PBS) with 0.1% Tween 20 (PBT). Primary antibodies were applied in blocking solution for 1 h at room temperature or over night at 4° C. Membranes were washed in PBT and incubated with corresponding secondary antibodies in 5% non fat dry milk in PBT for 1 h at room temperature. Cells were washed with PBT, incubated with ECL solution and exposed in a Fluorchem 5500 (Biozym, Oldendorf, Germany).

Concentration-Dependent Apoptosis Induction by Imiquimod® in OPM2 Cells:

OPM2 cells were suspended in full medium and cultured in 24-well plates at a cell density of 500.000 cells/ml and well. Cells were left untreated (control) or treated over night with different concentrations of Imiquimod® (10, 20 or 40 µg/ml). Subsequently, cells were harvested, lysed and the extent of apoptosis induction was determined by the analysis of PARP1 cleavage and IRAK1 and IκB-α degradation by Western blot. α-tubulin was used as a loading control.

Kinetics of Apoptosis Induction by Imiquimod® in OPM2 Cells:

OPM2 cells were cultured in 24-well plates as described above. Imiquimod® (40 µg/ml) was added to cells (except controls) for different time periods (2, 4, 6 and 8 h) and the extent of PARP1 cleavage, IRAK1, IkB-α and IkB-β degradation were determined by Western blot. α-Tubulin was used as a loading control.

Comparison of Apoptosis Induction by Imiquimod® and Gardiquimod®:

Cells were cultured as described before and, treated with 40 µg/ml Imiquimod® or Gardiquimod® for 24 h, and apoptosis was assayed by AnnexinV/PI staining and FACS analysis.

Test of Effect of Imiquimod® on Different Cell Lines/PBMCS:

Adherent cells were grown in 24-well plates to confluence and treated with 40 µg/ml Imiquimod® for 24 h. Cells were then trypsinized, suspended in full medium, stained for AnnexinV/PI and apoptosis was measured as described before. Suspension cells (250.000) were treated with 40 µg/ml Imiquimod® for 24 h, stained for Annexin/PI and apoptosis was measured as described above (Annexin V/Propidium Iodide apoptosis Assay).

Treatment of OPM2 Cells with Multiple Low Doses of Imiquimod®

$2 \times 10^5$ OPM2 cells in 1 ml of full medium were cultured in 24-well plates in duplicates for 8 days. For the first three days the appropriate amount of Imiquimod® (1, 2, 5, 5, or 10 µg/ml) was added daily. For determination of absolute cell numbers 100 µl of cell suspension were taken on days 1-5 and day 8 and cell number was determined using the CASY Cell Counter Model DT (Schärfe System GmbH, Reutlingen, Germany).

On the fourth day cells were spun down (200 g, 2 min) and 600 µl of the remaining 700 µl of supernatant (100 µl were left to keep cell pellet undisturbed) were removed and 600 µl of fresh full medium was added to the cell culture.

TABLE 1

Patient characteristics

| Initials | Age | Sex | Paraprotein | MM cells [%] | Stage* |
|---|---|---|---|---|---|
| R. M. | 69 | m | IgG-λ | 10 | 2 |
| O. F. | 84 | m | IgA-κ | 53 | 3 |
| S. A | 76 | f | IgG-κ | 25 | 1 |
| L. L. | 76 | m | k-light chain | 18 | 3 |
| R. A. | 81 | f | IgA-λ | 40 | 1 |
| G. A. | 72 | f | IgG-λ | 17 | 3 |

TABLE 1-continued

Patient characteristics

| Initials | Age | Sex | Paraprotein | MM cells [%] | Stage* |
|---|---|---|---|---|---|
| R. D. | 65 | m | IgG-λ | 30 | 1 |
| H. W. | 69 | m | IgG-κ | 60 | 3 |

*Clinical stage according to the ISS for multiple myeloma (Greipp et al, J Clin Oncol 2005)

Combination Therapy Assay:
Drugs/Inhibitors:

Thalidomide: used in multiple myeloma patients 100-400 mg/d[13]; source: Klinikapotheke Innsbruck, dissolved in DMSO Sorafenib® (BAY43-9006): used in various types of cancer[14], solution in DMSO Velcade: used in multiple myeloma patients 1.3 mg/m2[16], source: Klinikapotheke Innsbruck, dissolved in 0.9% NaCl GÖ6976: PKC-Inhibitor (Alexis Biochemicals, Lausen, Switzerland)[17], dissolved in DMSO SU1498: strong inhibitor of Flk-1, weak inhibitor of several other Receptor Tyrosine Kinases inhibitor ($IC_{50}$ 700 nM)[18], dissolved in DMSO Dexamethasone®: used in myeloma[19] source: Sigma, dissolved in 96% Ethanol.
Protocol:

OPM-2 and U266 cells ($2.5 \times 10^5$ in 500 µl) were treated with either Imiquimod® alone (10 µg/500 µl), various inhibitors/drugs alone or with the combination of Imiquimod® and inhibitors for 24 or 48 h. In the controls the solvent of the drug has been added in appropriate amounts. Cells were then AnnexinV/PI stained and apoptosis measured as described before.

Mouse Xenotranslplantation Model:

Xenotransplantation was performed as described previously[23] in particular $3 \times 10^7$ OPM-2 cells were suspended in full medium to a total volume of 100 µl and were mixed with 100 µl of Matrigel (Basement Membrane Matrix High Concentration (HC); BD-Biosciences, #354248) and injected into the right flanks of 5-6 week old NIH III-nude mice. Average tumor diameter and mouse body weight was measured every 3rd day.

Treatment was started when tumors reached an average diameter of 0.8 cm and mice were sacrificed when the tumor reached an average diameter of 1.5 cm. A maximum volume of 150 µl of Imiquimod®, in a concentration of 2.5 mg/ml in $H_2O$, was injected subcutaneously into the left flank of the mice. The same amount of $H_2O$ was injected in the same way into control mice. Tumor volume was calculated with the formula $4\pi/3 \times (width/2)2 \times (length/2)$.

EXAMPLE II

Induction of Apoptosis by Imiquimod® and Gardiquimod® in OPM2 Cells

To find out if multiple myeloma (MM) cells are sensitive to Imiquimod®, we treated OPM2 cells with different concentrations of Imiquimod® over night. The extent of apoptosis induced by this treatment was determined by Western blot analysis of poly (ADP-ribose) polymerase (PARP). Cleavage of PARP is an early and irreversible event in cells undergoing apoptosis[20]. Imiquimod® induced PARP cleavage in OPM2 cells in a concentration-dependent manner, with almost 100% of PARP cleavage at a concentration of 40 µg/ml of Imiquimod® (FIG. 1A). To analyse if the TLR7 pathway was activated we also analyzed IRAK1 and IκB-α proteins by Western blotting. IRAK1 is a downstream protein in the TLR7 signalling pathway which is phosphorylated and degraded upon TLR activation[21]. Comparable to PARP, IRAK1 was also degraded in a concentration-dependent manner upon Imiquimod® treatment of the cells. IκB-α binds to NF-κB and thereby inhibits the NF-κB activation and its migration of NF-κB to the nucleus. Upon activation, for example downstream of IRAK1 in the TLR signalling pathway, IκB-α is phosphorylated by IKK (I-κB kinase) and subsequently degraded by the proteasome, releasing and activating NF-κB[22]. Also IκB-α was degraded in a concentration dependent manner after Imiquimod® treatment of OPM2 cells, indicating NF-κB activation. This shows that the TLR signalling pathway was activated by similar concentrations of Imiquimod® by which apoptosis was induced.

To inquire the kinetics of the apoptosis induction by Imiquimod® OPM2 cells were treated with 40 µg/ml of Imiquimod® for different time periods. The fraction of apoptotic cells increased in a time-dependent manner, starting with some PARP cleavage 2 hours after Imiquimod® application and increasing to nearly complete PARP cleavage after 6 hours (FIG. 1B). Again the TLR downstream factors IRAK1, IκB-α and IκB-β were degraded at comparable kinetics.

To further test the involvement of TLR7 in apoptosis induction Gardiquimod® another, recently described TLR7 agonist was applied to OPM2 cells and apoptosis was measured by AnnexinV/PI staining and flow-cytometry after 24 h incubation. Also Gardiquimod® was able to induce apoptosis in OPM2 cells in a comparable, though slightly lower extend, as Imiquimod® (FIG. 1C).

EXAMPLE III

Imiquimod® Preferentially Induced Apoptosis in MM Cells

To test whether apoptosis induction by Imiquimod® was specific for multiple myeloma (MM) cells, several non-MM cell lines and peripheral blood mononuclear cells (PBMCs) from healthy volunteers were treated with 40 µg/ml Imiquimod® for 24 h and apoptosis was measured by AnnexinV/PI staining and flow cytometry analysis. Experiments with a set of adherent cell lines of different origin (details on cells are presented in the Materials and Methods section) showed only no significant or only minimal sensitivity to Imiquimod® (FIG. 2A). In contrast, all tested MM-cell lines (OPM2, U266, LP1, NCI) were sensitive, even though to a variable extend, ranging from mild apoptosis induction with about 30% of U266 cells dying upon Imiquimod® treatment to very high sensitivity of NCI cells with 90% apoptotic cells (FIG. 2B). This coincides with the general observation that U266 and LP1 cells are less sensitive to general induction of apoptosis than the other MM cell-lines tested. In addition, the suspension cell lines Raji, representing Burkitt's lymphoma, and Jurkat, representing acute T cell leukemia, showed if at all only low sensitivity to Imiquimod® (FIG. 2B).

PBMCs were isolated from 12 healthy donors as described in Material and Methods (example I) and the effect of Imiquimod® was measured. CD4+ and CD8+ cells exhibited nearly no sensitivity, while CD19+ cells were only mildly affected (FIG. 2C).

EXAMPLE IV

Effect of Multiple Low Doses of Imiquimod® on MM-Cells

Next, it was investigated if multiple low doses of Imiquimod® were also able to induce apoptosis and/or to inhibit cell growth. Therefore, OPM2 cells were treated daily with different low doses of Imiquimod® for three consecutive days. During and after treatment cells were counted (details in Materials and Methods) to establish a growth curve (FIG. 3, representative experiment). On the fourth day 600 of 700 µl of the medium were exchanged to remove the Imiquimod® and to analyse if the cell population is able to recover. It could clearly be shown that even multiple low doses of Imiquimod® decreased the growth potential of OPM2 cells in a concentration-dependent manner. A 3-times given dose of 10 µg/ml was sufficient to irreversibly inhibit cell growth. A triple treatment with 5 µg/ml was sufficient to significantly block the growth potential, however, some cells were able to recover from treatment.

EXAMPLE V

The Effect of Imiquimod® on MM-Cells from MM-Patient Bone Marrow Aspirates

In addition to the analysis of MM cell lines we tested the effect of Imiquimod® on primary myeloma cells isolated from the bone marrow of MM patients. The isolation procedure of bone marrow mononuclear cells (BMMCs) is described in detail in the Material and Methods section. Freshly isolated BMMCs, consisting of MM and non-tumor cells, were treated with 40 µg/ml Imiquimod® for 8 h or 24 h. After treatment the extent of apoptosis induction was quantified by flow cytometry. Briefly, cells were stained with Annexin V/PI together with fluorochrome-labelled antibodies to CD38 and CD45, which allowed separate analyses of tumor cells and bystander cells by gating on $CD38^{high}CD45^{low}$ and $CD38^{neg}CD45^{high}$ cells, respectively. As shown in FIG. 4, Imiquimod® significantly induced apoptosis in primary MM cells in a time dependent manner. We observed also induction of apoptosis by Imiquimod® in $CD45^{high}$ non-tumor cells suggesting a bystander effect on non-tumor leukocytes. This is in contrast to the very low sensitivity of PBMCs from healthy donors to Imiquimod® (see FIG. 3C). Since the NF-κB activation status influences TLR signaling, this difference in sensitivity of peripheral blood cells from healthy donors and BMMCs from myeloma patients might be explained by constitutive NF-κB activation in the latter as a result of the pro-inflammatory microenvironment generally observed in tumor patients and MM patients as well.

EXAMPLE VI

The Effect of Different Drugs/Inhibitors on Multiple Myeloma Cells in Combination with Imiquimod®/Combination Therapy Next apoptosis induction by different doses of cancer drugs/inhibitors alone or in combination with the suboptimal dose of 20 µg/ml of Imiquimod® was tested. The MM cell lines tested were OPM2 (see appended table 2A) and U266 (see appended table 2B) which showed comparable effects even though the effects were weaker in U266 cells. In the following paragraph for practical reasons only the effects on OPM2 cells are described. The cells were treated for 24 h and 48 h. In our experimental setting thalidomide and Dexamethasone® alone did not induce apoptosis at any dose tested, while Imiquimod® together with Thalidomide (1 mM) or Dexamethasone® (100 nM and 1 µM) induced more apoptosis after 48 h than Imiquimod® alone. Also the PKC inhibitor Gö6976 had nearly no effect on its own, but in combination with Imiquimod® increased the apoptosis inducing effect of the latter at a concentration of 1 µM and 5 µM after 24 h and 48 h. SU1498, a VEGF-receptor inhibitor with additional inhibitory effect on several other receptor tyrosine kinases, had only a very weak pro-apoptotic activity at the two higher concentrations on its own which added to the apoptosis induction of Imiquimod®. Sorafenib® induced no apoptosis in OPM2 cells at a concentration of 1 µM, was equally effective to Imiquimod® in inducing apoptosis at a concentration at 10 µM and completely killed cells at 50 µM. The combination of Imiquimod® with 10 µM Sorafenib®, in contrast to 10 µM Sorafenib® alone, induced apoptosis in nearly 100% of cells after 48 h. Melphalan induced apoptosis in a concentration-dependent manner at all concentrations tested (10 µM, 20 µM, 50 µM), which added well to the effect of Imiquimod® leading to nearly complete apoptosis induction in all cells at 20 µM and 50 µM Melphalan after 48 h. Velcade, a proteasome inhibitor indirectly inhibiting NF-κB activation, was the only substance tested which in combination with Imiquimod® showed reduced apoptosis induction. Inducing strong apoptosis at 10 ng/ml and 50 ng/ml after 48 h, this effect was reduced upon addition of Imiquimod® at a Velcade concentration of 10 ng/ml. This reflects the results obtained in the examples above and relating to the molecular analysis. Without being bound by theory, the Imiquimod®-induced apoptosis suggests NF-κB activation as important step for the pro-apoptotic activity of Imiquimod®.

EXAMPLE VII

Anti-Tumoral Activity of Imiquimod® Upon Systemic Application in Xenotransplanted Mice To test whether Imiquimod® was able to exert its apoptosis inducing effects in vivo, we injected OPM-2 cells together with Matrigel subcutaneously into the right flank of immunodeficient NIH III nude mice[23]. After subcutaneous tumors reached a well-defined and measurable size, i.e. at a diameter of 0.8 cm, treatment with Imiquimod® or $H_2O$, as a vehicle control, was started. Cell culture experiments had shown that repeated applications of 5 to 10 µg/ml Imiquimod® were sufficient to persistently block cell growth and to induce apoptosis. Therefore, 10 mg/kg Imiquimod® in $H_2O$ or comparable volumes of $H_2O$ alone were injected subcutaneously into the left flank twice daily. Mice were observed until tumor size reached an average diameter of 1.5 cm when mice were sacrificed. In vehicle treated animals rapid tumor growth was observed in all mice (FIG. 5A). In contrast, changes in tumor volume were more heterogeneous in Imiquimod® treated mice, ranging from tumor regression and stagnation, via slower growth to increase in tumor volume comparable to controls (FIG. 5B).

Survival of treated mice was significantly increased (p=0.027, t-test, FIG. 6A). Besides development of scars at the injection site, which was only observed in the treatment group, no obvious side effects could be observed. Weight development showed no difference in treated versus control mice (FIG. 6B). In 5 cases tumor regression was observed and treatment was stopped when neither further size reduction, nor tumor re-growth could be observed for at least one week (FIG. 6C, left pictures). Remnants of the tumor, probably extra cellular matrix and/or matrigel deposits, were visible even weeks after the end of tumor treatment (data not shown). In 3 out of 5 such cases the tumor started to grow again at the same position within 2 weeks after the end of treatment, while in the 2 other cases at least 3 months passed until relapse occurred, indicating either the occurrence of resistant clones or the necessity for a more prolonged or continuous administration of the drug for a better tumor control. Histological analysis of the tumors by haematoxylin and eosin staining revealed a homogenous and dense structure with occasional necrotic lesions in the periphery of the tumors of control mice (FIG. 6D, left picture). In tumors of Imiquimod® treated mice, regions of massive tissue destruction could be observed; mainly in central regions (FIG. 6D, right picture). Immunohistochemical analysis with antibodies recognizing cleaved-Caspase 3 revealed that cells flanking or present in these regions were highly apoptotic (data not shown). However, also in some treated tumors regions without obvious signs of tissue destruction were visible, indicating an insufficient penetration of the drug or existence of probably resistant tumor cell populations.

EXAMPLES VIII TO XI

Akt Inhibitors in Combination with Imiquimod®

During our studies we tested the effects of combinations of low doses of Imiquimod® with different concentrations of drugs currently used in/for MM-therapy as well as compounds under development for MM-therapy. Most of the combinations displayed favorable combinatory effects. However, simultaneous application of the Akt-inhibitor Akti 1/2 and Imiquimod® had an outstanding apoptosis inducing effect on MM cell lines. Further detailed studies were performed to learn more about this effect.

EXAMPLE VIII

The Effect of Different Akt-Inhibitors in Combination with Imiquimod®

We applied combinations of Imiquimod® with Akti1/2 and a second Akt inhibitor, AktX, to OPM2 cells and compared apoptosis induction (FIG. 7A). Apoptosis induction was measured by AnnexinV/PI FACS analysis. The efficiency of the inhibition of Akt phosphorylation was monitored by Western blotting with antibodies against phospho-Akt. Antibody for actin served as a loading control (FIG. 7B).

AktX and Akti1/2 both induced some apoptosis by themselves, as well as the rather low dose of 20 µg/ml Imiquimod®. However, if both were combined, nearly all cells died after 24 h, indicating a super-additive antitumoral effect. As can be seen in the Western blotting (FIG. 7B), both inhibitors indeed inhibited the phosphorylation of Akt.

EXAMPLE IX

The Effect of Akti1/2 in Combination with Imiquimod® in Different Multiple Myeloma Cell Lines To find out if the combinatory apoptosis enhancing effect of Imiquimod® and Akti1/2 was limited to OPM2 cells or a general effect in multiple myeloma cell lines, we applied the combination to different multiple myeloma cell lines. After 24 h apoptosis was measured with FACS analysis after AnnexinV/PI staining. Imiquimod® alone induced some apoptosis itself, as well as Akti1/2. In combination, even though the apoptosis measured in the different cell lines varied, a super-additive effect was detected in all cell lines (FIG. 8). The varying sensitivity of the different cell lines also correlated with our previous experiments with Imiquimod® alone.

EXAMPLE X

The Effect of Akti1/2 in Combination with Imiquimod® in Different Non-Multiple Myeloma Cell Lines Further we tested the sensitivity of non-myeloma cell lines treated with Imiquimod®, Akti1/2 or the combination. For this experiment we took cell lines representing either B-cell derived neoplasias (Raji, Daudi, Ramos) or T-cell derived neoplasias (Jurkat, C7H2). Imiquimod® induced apoptosis to some minor degree in all cell lines, but most in the OPM2 cells included as a control. Akti1/2 had only a mild effect on the cell lines, with the exception of Daudi. The combination, however, affected all cell lines to some extent, however the multiple myeloma cell line OPM2 was by far the most sensitive one (FIG. 9).

EXAMPLE XI

The Effect of Akti1/2 in Combination with Imiquimod® in Peripheral Blood Mononuclear Cells We also tested Imiquimod®, Akti1/2 and the combination on peripheral blood mononuclear cells (PBMCs) isolated from healthy donors in order to evaluate a possible general toxicity of the combination. OPM2 and U266 for comparison and PBMCs were incubated with Imiquimod®, effects of Akti1/2 or both for 48 h and apoptosis induction were monitored by AnnexinV/PI FACS analysis (FIG. 10). Even though PBMCs were as sensitive as U266 cells, OPM2 cells were much more sensitive.

TABLE 2A

Effects of apoptosis induction in OPM2 cells by different drugs/inhibitors alone or in combination with Imiquimod ®: + indicates the range of apoptosis induction, 0 for no, + for low and ++++ for very strong apoptosis induction. Underlined + indicates cases where the combination of drug and Imiquimod ® induced stronger apoptosis induction than each of the single compounds alone. Note that only the effect of Velcade is influenced negatively by Imiquimod ®, while the apoptosis induced by Imiquimod ® was maintained in all cases.

| Thalidomide | 10 µM | 100 µM | 1 mM | Imi 20 µg/ml | Imi + 10 µM | Imi + 100 µM | Imi + 1 mM |
|---|---|---|---|---|---|---|---|
| 24 h | 0 | 0 | 0 | + | + | + | + |
| 48 h | 0 | 0 | 0 | ++ | ++ | ++ | +++± |
| Dex.* | 10 nM | 100 nM | 1 µM | Imi 20 µg/ml | Imi + 10 nM | Imi + 100 nM | Imi + 1 µM |
| 24 h | 0 | 0 | 0 | + | + | + | + |
| 48 h | 0 | 0 | 0 | ++ | ++ | ++± | +++± |

TABLE 2A-continued

Effects of apoptosis induction in OPM2 cells by different drugs/inhibitors alone or in combination with Imiquimod ®: + indicates the range of apoptosis induction, 0 for no, + for low and ++++ for very strong apoptosis induction. Underlined + indicates cases where the combination of drug and Imiquimod ® induced stronger apoptosis induction than each of the single compounds alone. Note that only the effect of Velcade is influenced negatively by Imiquimod ®, while the apoptosis induced by Imiquimod ® was maintained in all cases.

| Gö 6976 | 100 nM | 1 μM | 5 μM | Imi 20 μg/ml | Imi + 100 nM | Imi + 1 μM | Imi + 5 μM |
|---|---|---|---|---|---|---|---|
| 24 h | 0 | 0 | 0 | + | + | +± | +± |
| 48 h | 0 | 0 | + | ++ | ++ | +++± | +++± |
| SU1498 | 1 μM | 10 μM | 50 μM | Imi 20 μg/ml | Imi + 1 μM | Imi + 10 μM | Imi + 50 μM |
| 24 h | 0 | + | + | + | + | +± | +± |
| 48 h | 0 | + | ++ | ++ | ++ | +++± | +++± |
| Sorafenib | 1 μM | 10 μM | 50 μM | Imi 20 μg/ml | Imi + 1 μM | Imi + 10 μM | Imi + 50 μM |
| 24 h | 0 | + | ++++ | + | + | + | ++++ |
| 48 h | 0 | ++ | ++++ | ++ | ++ | +++± | ++++ |
| Melphalan | 10 μM | 20 μM | 50 μM | Imi 20 μg/ml | Imi + 10 μM | Imi + 20 μM | Imi + 50 μM |
| 24 h | + | + | ++ | + | + | +± | ++ |
| 48 h | + | ++ | +++ | ++ | ++ | +++± | +++± |
| Velcade | 1 ng/ml | 10 ng/ml | 50 ng/ml | Imi 20 μg/ml | Imi + 1 ng/ml | Imi + 10 ng/ml | Imi + 50 ng/ml |
| 24 h | 0 | + | + | + | + | + | + |
| 48 h | 0 | +++ | +++ | ++ | ++ | ++ | +++ |

*Dexamethasone

TABLE 2B

Effects of apoptosis induction in U266 cells by different drugs/inhibitors alone or in combination with Imiquimod ®: + indicates the range of apoptosis induction, 0 for no, + for low and ++++ for very strong apoptosis induction. Underlined + indicates cases where the combination of drug and Imiquimod ® induced stronger apoptosis induction than each of the single compounds alone. Note that only the effect of Velcade is influenced negatively by Imiquimod ®, while the apoptosis induced by Imiquimod ® was maintained in all cases.

| Thalidomide | 10 μM | 100 μM | 1 mM | Imi 20 μg/ml | Imi + 10 μM | Imi + 100 μM | Imi + 1 mM |
|---|---|---|---|---|---|---|---|
| 24 h | 0 | 0 | + | + | + | + | + |
| 48 h | 0 | 0 | + | + | + | + | + |
| Dex.* | 10 nM | 100 nM | 1 μM | Imi 20 μg/ml | Imi + 10 nM | Imi + 100 nM | Imi + 1 μM |
| 24 h | 0 | 0 | 0 | + | + | + | + |
| 48 h | 0 | 0 | 0 | + | + | + | + |
| Gö 6976 | 100 nM | 1 μM | 5 μM | Imi 20 μg/ml | Imi + 100 nM | Imi + 1 μM | Imi + 5 μM |
| 24 h | 0 | 0 | 0 | + | + | +± | +± |
| 48 h | 0 | 0 | + | ++ | ++ | +++± | +++± |
| SU1498 | 1 μM | 10 μM | 50 μM | Imi 20 μg/ml | Imi + 1 μM | Imi + 10 μM | Imi + 50 μM |
| 24 h | 0 | + | + | + | + | +± | +± |
| 48 h | 0 | ++ | ++ | ++ | ++ | ++ | ++ |
| Sorafenib | 1 μM | 10 μM | 50 μM | Imi 20 μg/ml | Imi + 1 μM | Imi + 10 μM | Imi + 50 μM |
| 24 h | 0 | 0 | +++ | + | 0 | + | +++ |
| 48 h | + | + | +++ | + | + | +± | +++ |

TABLE 2B-continued

Effects of apoptosis induction in U266 cells by different drugs/inhibitors alone or in combination with Imiquimod ®: + indicates the range of apoptosis induction, 0 for no, + for low and ++++ for very strong apoptosis induction. Underlined + indicates cases where the combination of drug and Imiquimod ® induced stronger apoptosis induction than each of the single compounds alone. Note that only the effect of Velcade is influenced negatively by Imiquimod ®, while the apoptosis induced by Imiquimod ® was maintained in all cases.

| Melphalan | 10 µM | 20 µM | 50 µM | Imi 20 µg/ml | Imi + 10 µM | Imi + 20 µM | Imi + 50 µM |
|---|---|---|---|---|---|---|---|
| 24 h | + | + | ++ | + | + | +± | +++ |
| 48 h | + | + | +++ | + | +± | ++ | +++ |

| Velcade | 1 ng/ml | 10 ng/ml | 50 ng/ml | Imi 20 µg/ml | Imi + 1 ng/ml | Imi + 10 ng/ml | Imi + 50 ng/ml |
|---|---|---|---|---|---|---|---|
| 24 h | 0 | ++ | ++ | + | + | + | ++ |
| 48 h | 0 | +++ | +++ | ++ | + | ++ | ++ |

*Dexamethasone

Additional Literature

REFERENCES

1. Hallek, M., Bergsagel, P. L. & Anderson, K. C. Multiple myeloma: increasing evidence for a multistep transformation process. *Blood* 91, 3-21 (1998).
2. Esteve, F. R. & Roodman, G. D. Pathophysiology of myeloma bone disease. Best *Pract Res Clin Haematol* 20, 613-24 (2007).
3. Kyle, R. A. & Rajkumar, S. V. Multiple myeloma. *N Engl J Med* 351, 1860-73 (2004).
4. Takeda, K., Kaisho, T. & Akira, S. Toll-like receptors. *Annu Rev Immunol* 21, 335-76 (2003).
5. Diebold, S. S., Kaisho, T., Hemmi, H., Akira, S. & Reis e Sousa, C. Innate antiviral responses by means of TLR7-mediated recognition of single-stranded RNA. *Science* 303, 1529-31 (2004).
6. Heil, F. et al. Species-specific recognition of single-stranded RNA via toll-like receptor 7 and 8. *Science* 303, 1526-9 (2004).
7. Schon, M. P. & Schon, M. TLR7 and TLR8 as targets in cancer therapy. *Oncogene* 27, 190-9 (2008).
8. Chen, M., Griffith, B. P., Lucia, H. L. & Hsiung, G. D. Efficacy of S26308 against guinea pig cytomegalovirus infection. *Antimicrob Agents Chemother* 32, 678-83 (1988).
9. Sidky, Y. A. et al. Inhibition of murine tumor growth by an interferon-inducing imidazoquinolinamine. *Cancer Res* 52, 3528-33 (1992).
10. Savage, P. et al. A phase I clinical trial of imiquimod, an oral interferon inducer, administered daily. *Br J Cancer* 74, 1482-6 (1996).
11. Du, X., Poltorak, A., Wei, Y. & Beutler, B. Three novel mammalian toll-like receptors: gene structure, expression, and evolution. *Eur Cytokine Netw* 11, 362-71 (2000).
12. Hemmi, H. et al. Small anti-viral compounds activate immune cells via the TLR7 MyD88-dependent signaling pathway. *Nat Immunol* 3, 196-200 (2002).
13. Thompson, J. L. & Hansen, L. A. Thalidomide dosing in patients with relapsed or refractory multiple myeloma. *Ann Pharmacother* 37, 571-6 (2003).
14. Abou-Alfa, G. K. et al. Phase II study of sorafenib in patients with advanced hepatocellular carcinoma. *J Clin Oncol* 24, 4293-300 (2006).
15. Escudier, B. et al. Sorafenib in advanced clear-cell renal-cell carcinoma. *N Engl J Med* 356, 125-34 (2007).
16. Richardson, P. G. et al. A phase 2 study of bortezomib in relapsed, refractory myeloma. *N Engl J Med* 348, 2609-17 (2003).
17. Martiny-Baron, G. et al. Selective inhibition of protein kinase C isozymes by the indolocarbazole Go 6976. *J Biol Chem* 268, 9194-7 (1993).
18. Strawn, L. M. et al. Flk-1 as a target for tumor growth inhibition. *Cancer Res* 56, 3540-5 (1996).
19. Rajkumar, S. V. et al. Multicenter, Randomized, Double-Blind, Placebo-Controlled Study of Thalidomide Plus Dexamethasone Compared With Dexamethasone As Initial Therapy for Newly Diagnosed Multiple Myeloma. *J Clin Oncol* (2008).
20. Oliver, F. J. et al. Importance of poly(ADP-ribose) polymerase and its cleavage in apoptosis. Lesson from an uncleavable mutant. *J Biol Chem* 273, 33533-9 (1998).
21. Janssens, S. & Beyaert, R. Functional diversity and regulation of different interleukin-1 receptor-associated kinase (IRAK) family members. *Mol Cell* 11, 293-302 (2003).
22. Karin, M. & Ben-Neriah, Y. Phosphorylation meets ubiquitination: the control of NF-[kappa]B activity. *Annu Rev Immunol* 18, 621-63 (2000).
23. Catley, L., et al. Alkyl phospholipid perifosine induces myeloid hyperplasia in a murine myeloma model. *Exp Hematol* 35, 1038-1046 (2007).
24. Goldstein, D., et al. Administration of imiquimod, an interferon inducer, in asymptomatic human immunodeficiency virus-infected persons to determine safety and biologic response modification. *J Infect Dis* 178, 858-861 (1998).
25. Savage, P., et al. A phase I clinical trial of imiquimod, an oral interferon inducer, administered daily. *Br J Cancer* 74, 1482-1486 (1996).
26. Calleja, V, et al. Role of a novel PH-kinase domain interface in PKB/Akt regulation: structural mechanism for allosteric inhibition. *PLoS Biol.,* 7(1):17 (2009).
27. Logie L., et al. Characterization of a protein kinase B inhibitor in vitro and in insulin-treated liver cells. *Diabetes* 56(9): 2218-27 (2007).
28. Barnett S. F., et al. Identification and characterization of pleckstrin-homology-domain-dependent and isoenzyme-specific Akt inhibitors. *Biochem J.* 385:399-408 (2005).
29. DeFeo-Jones, D., et al. Tumor cell sensitization to apoptotic stimuli by selective inhibition of specific Akt/PKB family members. *Mol Cancer Ther.* 4(2):271-9 (2005).
30. Zhao, Z., et al. Discovery of 2,3,5-trisubstituted pyridine derivatives as potent Akt1 and Akt2 dual inhibitors. *Bioorg Med Chem. Lett.,* 15(4):905-9 (2005).

31. Lindsley C. W., et al. Allosteric Akt (PKB) inhibitors: discovery and SAR of isozyme selective inhibitors. *Bioorg Med Chem. Lett.*; 15(3):761-4 (2005).
32. Thimmaiah, K. N., et al. Identification of N10-substituted phenoxazines as potent and specific inhibitors of Akt signaling *J. Biol. Chem.* 280, 31924 (2005).
33. Staal, S. P. Molecular cloning of the akt oncogene and its human homologues AKT1 and AKT2: amplification of AKT1 in a primary human gastric adenocarcinoma. *Proc Natl Acad Sci USA* 84, 5034-5037 (1987).
34. Garofalo, R. S., et al. Severe diabetes, age-dependent loss of adipose tissue, and mild growth deficiency in mice lacking Akt2/PKB beta. *J Clin Invest* 112, 197-208 (2003).
35. Yang, Z. Z., et al. Physiological functions of protein kinase B/Akt. *Biochem Soc Trans* 32, 350-354 (2004).
36. Strasser-Wozak, E. M., et al. Splice site mutation in the glucocorticoid receptor gene causes resistance to glucocorticoid-induced apoptosis in a human acute leukemic cell line. *Cancer Res* 55, 348-353 (1995).
37. Klein, S, and Levitzki, A. Targeting the EGFR and the PKB pathway in cancer. *Curr Opin Cell Biol.* 21(2):185-93 (2009).
38. Schon, M., et al. Tumor-selective induction of apoptosis and the small-molecule immune response modifier imiquimod. *J Natl Cancer Inst* 95, 1138-1149 (2003).
39. Schon, M. P., et al. Death receptor-independent apoptosis in malignant melanoma induced by the small-molecule immune response modifier imiquimod. *J Invest Dermatol* 122, 1266-1276 (2004).
40. Song G, Ouyang G, Bao S. The activation of Akt/PKB signaling pathway and cell survival. *J Cell Mol. Med.* 9(1): 59-71 (2005).

The invention claimed is:

1. A method for the treatment and/or amelioration of a haematological cancer, wherein said method comprises the administration of a pharmaceutically active dose of a compound as defined in formula I to a subject in the need of such a treatment and/or amelioration, wherein said compound is to be administered to the subject in need of such a treatment in combination with an Akt inhibitor, and wherein formula I is

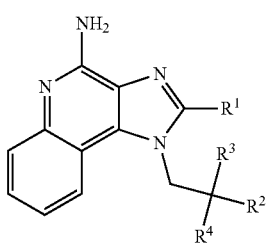

I wherein
$R^1$ is H or —$CH_2$—$NR^5$—$(CH_2)_m$—$CH_3$, whereby m is an integer of 0 to 3 and $R_5$ is H or $C_1$-$C_4$ alkyl; and
$R^2$, $R^3$, $R^4$ are independently selected from H, $C_1$-$C_4$ alkyl, OH, $NH_2$, CN, Cl, Br, I or F, or a pharmaceutically acceptable salt, derivative or prodrug thereof.

2. The method of claim 1, wherein the subject is a human patient.

3. The method of claim 1, wherein two of $R^2$—$R^4$ are $C_1$-$C_4$ alkyl and the remaining is H.

4. The method of claim 3, wherein $R^1$ is H.

5. The method of claim 1, wherein two of $R^2$—$R^4$ are $C_1$-$C_4$ alkyl and the remaining is OH.

6. The method of claim 5, wherein $R^1$ is —$CH_2$—NH—$C_2H_5$.

7. The method of claim 1, wherein said compound has the following formula II:

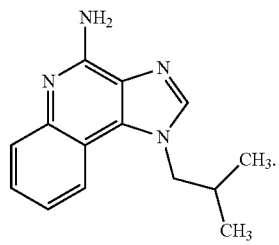 [SMILES: CC(C)Cn1cnc2c(N)nc3ccccc3c21]

8. The method of claim 1, wherein said compound has the following formula III:

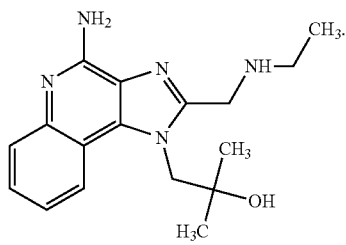 [SMILES: CCNCc1nc2c(N)nc3ccccc3c2n1CC(C)(C)O]

9. The method of claim 1 wherein said Akt inhibitor is of the following formula IV:

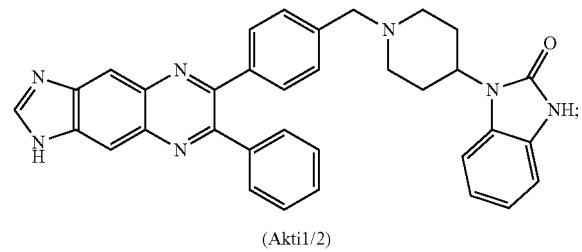 [SMILES: O=c1[nH]c2ccccc2n1C1CCN(Cc2ccc(-c3nc4cc5nc[nH]c5cc4nc3-c3ccccc3)cc2)CC1]

(Akti1/2)

or of the following formula V:

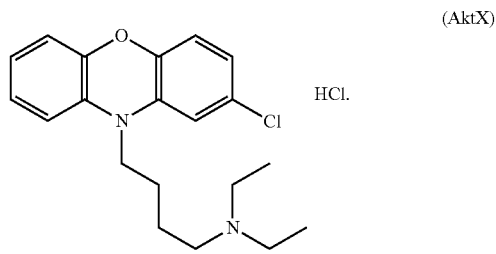

(AktX)

10. The method of claim 1, wherein said haematological cancer is multiple myeloma.

* * * * *